(12) United States Patent  
Menon et al.

(10) Patent No.: US 9,063,189 B2  
(45) Date of Patent: Jun. 23, 2015

(54) MAGNETIC RESONANCE SYSTEM AND METHOD TO DETECT AND CONFIRM ANALYTES

(75) Inventors: Suresh M. Menon, San Diego, CA (US); David E. Newman, Fallbrook, CA (US); Steven C. Chan, San Diego, CA (US)

(73) Assignee: Menon Biosensors, Inc., San Diego, CA (US)

( * ) Notice: Subject to any disclaimer, the term of this patent is extended or adjusted under 35 U.S.C. 154(b) by 0 days.

(21) Appl. No.: 13/605,539

(22) Filed: Sep. 6, 2012

(65) Prior Publication Data

US 2013/0059293 A1    Mar. 7, 2013

Related U.S. Application Data

(63) Continuation of application No. 11/549,064, filed on Oct. 12, 2006, now abandoned.

(60) Provisional application No. 60/759,788, filed on Jan. 19, 2006, provisional application No. 60/786,033, filed on Mar. 27, 2006.

(51) Int. Cl.
*G01R 33/12* (2006.01)
*B82Y 25/00* (2011.01)
*G01R 33/465* (2006.01)
*G01R 33/30* (2006.01)
*G01N 24/08* (2006.01)
*G01R 33/44* (2006.01)

(52) U.S. Cl.
CPC .............. *G01R 33/12* (2013.01); *Y10T 436/24* (2015.01); *B82Y 25/00* (2013.01); *G01N 24/084* (2013.01); *G01R 33/1269* (2013.01); *G01R 33/1276* (2013.01); *G01R 33/448* (2013.01); *G01R 33/465* (2013.01); *G01R 33/307* (2013.01)

(58) Field of Classification Search
None
See application file for complete search history.

(56) References Cited

U.S. PATENT DOCUMENTS

| 4,745,077 A | 5/1988 | Holian et al. |
| 4,875,486 A | 10/1989 | Rapoport et al. |
| 4,969,469 A | 11/1990 | Mills |
| 5,108,933 A | 4/1992 | Liberti et al. |
| 5,254,460 A * | 10/1993 | Josephson et al. ........... 435/7.25 |
| 5,445,970 A | 8/1995 | Rohr |
| 5,445,971 A | 8/1995 | Rohr |

(Continued)

FOREIGN PATENT DOCUMENTS

| SU | 1073654 A | 2/1984 |
| WO | 0111360 A2 | 2/2001 |

(Continued)

OTHER PUBLICATIONS

Supplementary European Search Report for EP06849669.4, issued Sep. 8, 2009, 7 pages.

(Continued)

*Primary Examiner* — Robert T Crow
(74) *Attorney, Agent, or Firm* — Procopio, Cory, Hargreaves & Savitch LLP

(57) ABSTRACT

A system and method are provided to detect target analytes based on magnetic resonance measurements. Magnetic structures produce distinct magnetic field regions having a size comparable to the analyte. When the analyte is bound in those regions, magnetic resonance signals from the sample are changed, leading to detection of the analyte.

11 Claims, 18 Drawing Sheets

(56) References Cited

U.S. PATENT DOCUMENTS

| | | | |
|---|---|---|---|
| 5,536,644 | A | 7/1996 | Ullman et al. |
| 5,773,307 | A | 6/1998 | Colin et al. |
| 5,925,573 | A | 7/1999 | Colin et al. |
| 5,981,297 | A | 11/1999 | Baselt |
| 5,998,224 | A | 12/1999 | Rohr et al. |
| 6,013,188 | A | 1/2000 | Terstappen et al. |
| 6,020,211 | A | 2/2000 | Tuunanen |
| 6,143,577 | A | 11/2000 | Bisconte Sconte De Saint Julien |
| 6,143,578 | A | 11/2000 | Bendele et al. |
| 6,159,378 | A | 12/2000 | Holman et al. |
| 6,294,342 | B1 | 9/2001 | Rohr et al. |
| 6,342,396 | B1 | 1/2002 | Perrin et al. |
| 6,500,343 | B2 | 12/2002 | Siddiqi |
| 6,511,967 | B1 | 1/2003 | Weissleder et al. |
| 6,548,264 | B1 | 4/2003 | Tan et al. |
| 6,623,982 | B1 | 9/2003 | Liberti et al. |
| 6,630,355 | B1 | 10/2003 | Pivarnik et al. |
| 6,649,419 | B1 | 11/2003 | Anderson |
| 6,767,635 | B1 | 7/2004 | Bahr et al. |
| 6,852,493 | B2 | 2/2005 | Ramirez-Vick et al. |
| 6,972,095 | B1 | 12/2005 | Bushart et al. |
| 7,018,849 | B2 | 3/2006 | Piasio et al. |
| 7,781,228 | B2 * | 8/2010 | Menon et al. ............. 436/526 |
| 2002/0062702 | A1 * | 5/2002 | Bradley ............. 73/864.34 |
| 2003/0092029 | A1 | 5/2003 | Josephson et al. |
| 2003/0216638 | A1 | 11/2003 | Dharmakumar et al. |
| 2004/0038255 | A1 * | 2/2004 | Mirkin et al. ............. 435/6 |

FOREIGN PATENT DOCUMENTS

| | | |
|---|---|---|
| WO | 02098364 A2 | 12/2002 |
| WO | 2005099419 A2 | 10/2005 |
| WO | 2005/124345 A2 | 12/2005 |

OTHER PUBLICATIONS

Routley et al. "The Halo system—a light weight portable imaging system." Magnetic Resonance Imaging. 22(8):1145-1151 (Oct. 1, 2004). XP004641706, ISSN: 0730-725X.

File history for United States Reexamination Control No. 95/001,541, filed Feb. 8, 2011 (Inter Partes Reexamination of U.S. Patent No. 7,781,228), in 635 pages.

Perez et al. "Use of Magnetic Nanoparticles as Nanosensors to Probe for Molecular Interactions." ChemBioChem. 5:261-264 (Feb. 26, 2004), XP002418115.

Extended European Search Report issued on Nov. 17, 2011, in European Patent Application No. 07868161.6 in 9 pages.

Dubus et al. "PCR-Free DNA Detection Using a Magnetic Bead-Supported Polymeric Transducer and Microelectromagnetic Traps." Anal. Chem. 78(13):4457-4464 (2006).

International Search Report and Written Opinion from PCT/US06/02368 mailed Jul. 28, 2008.

Grimm et al. "Novel Nanosensors for Rapid Analysis of Telomerase Activity." Cancer Research. 64:639-643 (Jan. 15, 2004).

Perez et al. "Magnetic relaxation switches capable of sensing molecular interactions." Nature Biotechnology. 20:816-820 (Aug. 2002).

Massin et al. "Planar microcoil-based microflouride NMR probes." Journal of Magnetic Resonance. 164:242-255 (2003).

Lee et al. "Microelectromagnets for the control of magnetic nanoparticles." Applied Physics Letters. 79 (26):3308-3310 (Nov. 12, 2001).

International Search Report and Written Opinion for PCT/US07/60696, mailed Sep. 16, 2008, 18 pages.

Fallesen et. al., "Magnet polepiece design for uniform magnetic force on superparamagnetic beads" Rev. Sci. Instruments 81, 074303 (2010).

"Surface plasmon resonance", Wikipedia, viewed at http://en.wikipedia.org/wiki/Surface_plasmon_resonance on Jun. 23, 2014.

"Paramagnetism", Wikipedia, viewed at http://en.wikipedia.org/wiki/Paramagnetism on Jun. 23, 2014.

"Biopharmaceutical Assays & Screening glossary & taxonomy," viewed at http://www.fluidigm.jp/gloss/gloss_homogeneous.htm, last updated Mar. 5, 2014.

Callaghan "Principles of Magnetic Resonance Microscopy", p. 45-46 (Oxford Science Publications, New York. 1991).

Database WPI Week 198441, 1984. Thomson Scientific, London, GB. AN 1984-255506. XP002724195.

Extended European Search Report for related EP Patent Application No. 14163943.5, dated Jun. 4, 2014, in 9 pages.

GIJS. "Magnetic bead handling on-chip: new opportunities for analytical applications." Microfluid Nanofluid. 1:22-40 (2004).

* cited by examiner

FIGURE 8a-d

MAGNETIC RESONANCE SYSTEM AND METHOD TO DETECT AND CONFIRM ANALYTES

RELATED APPLICATIONS

This application is a continuation of U.S. patent application Ser. No. 11/549,064, filed Oct. 12, 2006, titled "MAGNETIC RESONANCE SYSTEM AND METHOD TO DETECT AND CONFIRM ANALYTES," which is hereby incorporated by reference, which claims the benefit of U.S. provisional application Ser. No. 60/759,788, filed Jan. 19, 2006, titled MAGNETIC ENHANCEMENT OF NANO-PARTICLE REACTIONS, and Ser. No. 60/786,033, filed Mar. 27, 2006, titled MAGNETIC CONCENTRATION OF REAGENTS both of which are hereby incorporated by reference.

GOVERNMENT INTEREST

This invention was made with U.S. Government support under one or more of the following contracts: Naval Air Warfare Center n68335-02-c-3120, Department of Homeland Security contracts NBCHC060017 and HSHQPA-05-9-0039. The U.S. Government has certain rights in this invention.

BACKGROUND

1. Field of the Invention

The present invention generally relates to the field of analyte detection and additionally relates to detecting analytes using magnetic resonance.

2. Related Art

Detection technology for specific analytes spans a wide range of laboratory instrumentation and techniques including liquid and gas chromatography (LC and GC, respectively), mass spectrometry (MS), nuclear magnetic resonance (NMR) spectroscopy, polymerase chain reaction (PCR), optical spectroscopy and fluoroscopy, Fourier transform infrared (FTIR) spectroscopy, and ion mobility instruments. Today's chemical analysis instruments however, are large and expensive, require a skilled operator, involve complex sample preparation, and require substantial amounts of time for analysis.

There is a critical need worldwide for improved detection of specific chemicals and microbes. For example, in the area of national security, a system is needed to detect biological agents, toxins, and chemical weapons to provide early alert in case of a terrorist attack. Such a detection capability could also be used to search for clandestine sites where such weapons are under development or in production, thus enabling action to prevent their use. A system is also needed to scan mail and packages to detect a terrorist attack.

Improved pathogen detection is also needed for medical science. Sensitive detection of DNA or proteins associated with avian flu, bovine spongiform encephalopathy (more commonly referred to as "mad-cow disease"), or severe acute respiratory syndrome (SARS) would enable intervention to avoid a pandemic. Broad clinical use of such a system would assist in identifying ordinary diseases or serious illnesses, greatly assisting physicians in diagnosis.

Detection of various chemicals is also needed for industrial applications to detect toxic industrial chemicals (TICs) and toxic industrial materials (TIMs). Such a system would enable leak detection, process control, detection of material degradation, control of concentration, and a host of other process applications in a wide range of industries.

Improved detection is also needed in agriculture and food production, as well as a means to detect contamination, spoiling, or poisoning of food. Food includes for example, items such as drinking water and fruit juices. There is also a need in forensic testing, including for example, searching for specific DNA sequences in a sample at the search site.

Magnetic resonance detection techniques are under development involving nanometer-scale paramagnetic particles (nanoparticles) which have previously been used as MRI contrast agents. The particles comprise a core of paramagnetic or superparamagnetic (both generally referred to herein as paramagnetic) material, coated by a shell of nonmagnetic material which are adorned with reactant molecules to promote binding to target cells such as pathogens, tumor cells, etc. Nanoparticles are injected into a patient prior to MRI analysis. They bind to the target cells, cause a local change in the MRI image properties, and enable detection or localization of the target cells.

The nanoparticles have also been used in vitro. Dissolved or suspended in a liquid medium, the nanoparticles bind to target cells or molecules in the medium. The nanoparticles and analytes may form aggregates incorporating dozens to thousands of nanoparticles. Such aggregates are detectable by light scattering, atomic-force microscopy, electron microscopy, and in some cases by NMR effects. See, for example, U.S. Pat. No. 5,254,460 to Josephson et al.

Target-specific reactants can be mounted onto the nanoparticles to provide analyte-specific selectivity. A disadvantage is the need to form aggregations comprising a plurality of nanoparticles and a plurality of target cells or molecules, because aggregation occurs only when each nanoparticle is bound to multiple analytes, and each analyte is bound to multiple nanoparticles. Aggregation can be inhibited by geometrical effects such as a variation in size among nanoparticles. Substantial time may be required for the aggregations to form.

Prior studies on agglomeration were conducted on bench-top relaxometers and high-field MR instruments. Manual sample preparation and insertion into the NMR tube can be tedious. Important events such as binding of the analyte to the nanoparticles may be missed. A compact and automated instrument is required to speed up measurements. Also, it is important to understand the phenomena describing the changes seen in the measurement from a basic physics and biochemistry standpoint.

Earlier studies did not model the change in T2 effects from a physics standpoint. Simple agglomeration effects were observed through optical means (microscopes) to establish the phenomena relating change in T2. In addition, early studies did not take advantage of stoichiometry control of the nanoparticles to adapt the measured parameters for various applications leading to specific NMR products.

Earlier studies used samples that were pure and not subject to interferences such as dust, acids, etc. Moreover, there was no requirement for fast measurements combined with no interference from clutter and near neighbor molecules, cost of overall system, low false alarms and high probability of detection. There was also no defined range of analyte concentrations to be detected.

Earlier studies did not consider use of improved paramagnetic materials such as compounds of iron, cobalt and nickel leading to stronger magnetization and improved sensitivity. Earlier studies did not consider use of magnetic fields to influence interactions between nanoparticles or between molecules attached to nanoparticles. Use of magnetic fields to control the formation or geometrical configuration of structures comprising nanoparticles and analytes has not been considered. Use of magnetic fields to concentrate reactants so as to accelerate selected interactions was not previously considered.

SUMMARY

A system and method are provided which can detect target analytes based on magnetic resonance measurements. In one aspect analytes are detected using specific nanoparticles in the form of magnetic resonance nanoswitches. The reaction between the nanoparticles and analytes is controlled through the application of a magnetic field.

In one aspect, a system and method for detecting an analyte include attaching nanoparticles to the analyte, thereby forming nanoparticle-analyte complexes. A magnetic field is applied to the complexes in a known liquid, thereby magnetizing the nanoparticles. The magnetic field exerts forces on the nanoparticles, and the nanoparticles exert magnetic forces on each other. The complexes undergo motions responsive to the magnetic forces. The complexes undergo interactions, which interactions are enhanced by the motions. Magnetic resonance signals are excited from a sample comprising the complexes and the known liquid. A magnetic resonance parameter such as the T2 of the sample is determined from the magnetic resonance signals. Then, the system determines whether the analyte is present in the sample by analyzing the determined parameter and a predetermined value.

In one aspect of the invention, systems and methods detect targeted analytes with very high specificity, despite near-neighbor interference, dirt, clutter, biological interferents such as mold spores, proteinaceous interferents such as skim milk and ova albumin, paramagnetic interferents such as hemoglobin and humic acid (containing chelated iron), environmental interferents such as the so-called Arizona dust, diesel soot, etc.

One aspect of the invention includes a system and method for detecting analytes in a liquid medium. In another aspect analytes may be introduced as aerosol, hydrosol, and in complex media such as food.

The system includes a magnetic resonance system to detect resonance signals from the liquid, a magnetic field passing through that liquid, and a region within the liquid where the magnetic field has a distinct property such as a particular value or gradient. Liquid within that region produces magnetic resonance signals which depend on the field property, and liquid outside that region may also be influenced by the region due to diffusion. A material having particular affinity for the analyte is adjacent to the region. The analyte binds to or is held by the affinity material and displaces liquid from that region, thus altering the magnetic resonance signals and revealing the analyte.

A system for detecting an analyte comprises: a sample which contains the analyte within a liquid medium, means for generating a first magnetic field within the liquid, means for generating a second magnetic field within a special region within the liquid, means for holding the analyte within the special region, a magnetic resonance instrument capable of measuring magnetic resonance signals from the liquid, and means for analyzing those signals to determine whether the liquid occupies the special region. The second magnetic field is distinct from the first magnetic field. Magnetic resonance signals from the liquid residing within the special region respond to the second magnetic field, which causes magnetic resonance signals which differ detectably from signals of the liquid located exterior to the special region. In addition, liquid may pass through the special region and then return to the rest of the liquid, thereby influencing the magnetic resonance signals of the remaining liquid. In addition, liquid in the special region responds to the second magnetic field, for example by becoming depolarized, and then communicates that depolarization to the rest of the liquid through spin diffusion. When present, an analyte displaces liquid from the special region. Thus if the signals show that liquid occupies the special region, analyte must be absent. If the signals show that the liquid is displaced from the special region, then the analyte must be present, and is thus detected.

The analyte can be any molecule, molecular complex, microbe, chemical, or material which can be contained in the liquid medium, and which displaces the liquid when so contained. Examples of analytes include bio-molecules such as proteins, DNA, RNA, or fragments or complexes thereof; enzymes, small molecules, organisms, microbes such as whole or disrupted viruses or bacteria; whole or disrupted cells from other species including humans, non-biological chemicals such as chemical weapon molecules, explosives, insecticides, pharmaceuticals, and industrial chemicals.

In one embodiment the liquid contains the analyte. Here "contains" means that the analyte is dissolved, suspended, emulsified, or otherwise wholly enclosed in and dispersed within the liquid. Also, the analyte displaces the liquid, meaning that molecules of the analyte can not co-occupy space with molecules of the liquid.

The liquid can be any fluid material that includes a nucleus having non-zero spin. Only nuclei with non-zero spin give rise to the NMR phenomena. The liquid includes such nuclei when molecules comprising the liquid comprise a nucleus with non-zero spin, such as hydrogen in the water molecule. Alternatively, the liquid may include such nuclei as solutes or suspensions, such as a fluoridated solute which generates magnetic resonance signals at the $^{19}F$ Larmor frequency.

In a further aspect a system includes a first magnetic field which passes through the liquid. The first magnetic field may be produced by an electromagnet, permanent magnet, superconducting coil, or any other source. Normally the first magnetic field is a static and substantially uniform magnetic field that can be in the range of 0.01 Tesla to 20 Tesla, and is a part of the magnetic resonance system.

A second magnetic field is generated in a special region of the sample. The second magnetic field is distinct from the first magnetic field in some parameter that is detectable using magnetic resonance. For example, the second magnetic field may differ from the first magnetic field in magnitude, orientation, uniformity, gradient, or any other detectable parameter. A second magnetic field generator or means for generating the second magnetic field may be a nanoparticle, which may be suspended in the liquid and immersed in the first magnetic field or applied field. In one embodiment the nanoparticle becomes magnetized and produces a dipole-shaped field that adds vectorially to the applied field, producing a net magnetic field. The special region is that volume occupied by the distinct magnetic field. When the distinct magnetic field is caused by a nanoparticle, the special region is that nanometer-scale volume adjacent to but exterior to the surface of the nanoparticle, where the net field differs substantially from the applied magnetic field. Alternatively, the special magnetic field region could be produced by paramagnetic ions such as chelated iron or gadolinium instead of nanoparticles. An advantage of this approach is that diffusion-limited reaction rates may be increased due to the higher mobility of metal-ion chelates. Similar ions are used in MRI (Gd-DTPA and Gd-DOTA.).

Alternatively, the special magnetic field region is produced by particles or structures having a size larger than nanometer-scale, provided that the magnetic resonance signals differ detectably when analyte is present or absent. For example, shaped magnetic structures may provide two specific values of the magnetic field in two regions, and the analyte binding molecules could be coupled to only one of the field regions. The detection measurement is then a spectral analysis of the composite magnetic resonance signal, which will exhibit two frequency peaks corresponding to the two field regions when no analyte is present, or only a single peak when analyte obscures one of the field regions.

In one aspect, temperature cycling is used to accelerate binding between the analyte and nanoparticle. This shortens the binding event time by increasing the mobility of the analyte and/or the nanoparticle. When an energy barrier inhibits binding, higher temperatures improve the rate of binding. Temperature cycling may include heating and cooling or vice versa. Then the sample is measured in the magnetic resonance instrument.

In one aspect, the system includes a mechanism or binding agent for holding the analyte in the special region, to displace the liquid from the special region, leading to detection of the analyte. Such a binding agent can include any material surface or molecule for which the analyte has an affinity. Such holding may be accomplished by hydrogen bonds, ionic forces, covalent bonds, sulfide bridges, van der Waals forces, electrostatic forces, or any other type of molecular or material attachment or affinity ligand. The binding agent is positioned adjacent to the region of shaped magnetic field so that the target molecule, when bound, occupies that region and excludes the liquid therefrom. For example, the binding agent may be an antibody raised against an analyte protein, or DNA complementary to analyte DNA sequences. Preferably the binding agent also has null affinity or negative affinity for all solutes other than the analyte that may be present. In addition to DNA, other holding means can be used such as aptamers, small molecules, etc. Targets include, but are not limited to the following:

a. An antibody that recognizes and binds to an antigen
   b. an oligonucleotide or DNA sequence complementary to a DNA- or RNA-target
   c. a DNA- or RNA-aptamer that binds to a target protein, bacteria, virus, yeast or fungus.
   d. a protein or peptide that binds to a target protein, bacteria, virus, yeast or fungus.
   e. a pseudopeptide composed of unnatural amino acids with a stronger binding to a target or better environmental stability.
   f. a small molecule or combination of small molecules that can bind to a target.
   g. monosacharides, polysacharides, carbohydates and sugars that can bind to a target protein, bacteria, virus, yeast or fungus.

A further aspect includes a magnetic resonance instrument, which is capable of exciting and detecting magnetic resonance signals from the liquid medium. Existing magnetic resonance systems may perform this function. More preferably, the instrument is a simple, compact, automated, single-purpose magnetic resonance system which can perform the detection measurement automatically. The system measures signals related to the presence or absence of liquid, affected by the second magnetic field in the special region. For example, when the magnitude of magnetic field in the special region differs from that in the rest of the liquid, then the magnetic resonance system can measure the spectral content of the magnetic resonance signals to determine the magnetic field from which the signals emerged. Thus by analyzing for the Larmor frequency of the liquid in the special region, the system determines whether liquid occupies that region.

An alternative measurement is the spin-spin dephasing time (T2) of the liquid. T2 is affected when the magnetic field in the special region has strong gradients, and particularly when the liquid diffuses through those gradient fields in times short compared to the measurement. Thus the system can determine the presence of analyte by measuring the T2 of the liquid to determine if depolarization is occurring in the special region.

In one aspect, the compact magnetic resonance system can measure either a positive or negative change in T2. Agglomeration is described in the Josephson patent as the formation of a large supermolecular assembly of molecules. In the case of agglomeration, all measurements show a negative T2 change. Likewise, the parameter defined as "positive 1/T2" in Josephson represents a negative change in T2. Agglomeration is described by Josephson as a process where several molecules attach to each other and they form assemblies large enough to change the T2 of the water. In one embodiment, the inventive system measures T2 changes due to the analyte binding event, leading to positive and negative T2 changes prior to agglomeration.

In a further aspect, a system includes a magnetic field to control interactions involving nanoparticles and analytes. The analytes bind to the nanoparticles, producing nanoparticle-analyte binaries. A magnetic field is applied to the binaries. The magnetic field magnetizes the nanoparticles, the magnetization direction being substantially parallel to the magnetic field direction. The magnetized nanoparticles exert magnetic forces called dipole-dipole forces on each other. The forces can be mutually attractive, repulsive, or torsional depending on the relative positions of the nanoparticles and the magnetic field direction. When a line between two nanoparticles is parallel to the field direction, the mutual magnetic force is attractive. When a line between two nanoparticles is perpendicular to the field direction, the force is repulsive. At all other orientations, the nanoparticles exert mutual torsional forces on each other, and the torsional forces are such as to drive the nanoparticles into parallel alignment with the field.

In one aspect, the magnetic field is substantially uniform throughout the sample volume. The magnetic field, through induced dipole-dipole forces between nanoparticles, urges the nanoparticle-analyte binaries into alignment with the magnetic field. The nanoparticles or the analytes interact when so aligned, producing for example a linear chain-like structure. The forces also drive the nanoparticles away from the perpendicular orientation. Nanoparticles are in the perpendicular orientation when a line between the nanoparticles is perpendicular to the magnetic field. The forces between nanoparticles thus suppress interactions in the perpendicular orientation, leading to suppression of three-dimensional aggregate structures.

In one aspect, the magnetic field is substantially non-uniform in the sample volume. The strength or magnitude of the non-uniform magnetic field varies throughout the sample volume. Preferably the magnetic field has maximal strength in a small subvolume of the sample volume. The magnetic field generates a force on the nanoparticles in addition to the mutual dipole-dipole forces between nanoparticles, the additional force being such as to draw the nanoparticles toward the region having the highest magnetic field magnitude. Responsive to that force, the nanoparticles or binaries drift toward the subvolume, thereby greatly increasing the concentration of the nanoparticles or binaries in that subvolume and depleting the concentration in the remainder of the sample volume.

Since many chemical interactions exhibit reaction rates which depend on the concentration of reactants, interactions between the nanoparticles or analytes or binaries can be accelerated in the subvolume, and inhibited in the rest of the sample volume.

In one aspect, the compact magnetic resonance system measures a baseline value of T2 using the nanoparticles or nanoparticle solution prior to analyte-nanoparticle binding. Analyte is then mixed with the nanoparticles or allowed to interact with the nanoparticles, and then the T2 of the sample is measured again to determine whether a change in T2 has occurred. The baseline measurement ensures the correct concentration of nanoparticles and consistent stoichiometry. Comparison of the baseline and subsequent T2 measurements enables cancellation of metering and mixing errors, variations in nanoparticle properties, fluidic transport errors, etc.

In one embodiment the inventive system can detect analyte by measuring magnetic resonance signals from the sample at a single time. Alternatively, the system can perform a series of measurements spanning a period of time and can compare or analyze the measurements to improve the detection of analyte. For example, the binding between analyte and nanoparticles may proceed during an interval which is longer than the time required for a particular measurement. Then the system can perform the measurements repeatedly to observe the changes caused by the binding. As another example, the analyte may first bind to nanoparticles to form binaries, causing a positive shift in T2. Then the binaries may combine to form agglomerates, causing a negative shift in T2. Such data can greatly enhance the quality of the result by reducing the false alarm rate, providing a lower detection threshold, and enhancing the detection probability for a given quantity of analyte.

In one aspect the system can derive parameters related to reaction rates or kinetics from repeated measurements on the same sample. For example, a rate of change of a measured parameter may indicate a rate of binding or other interaction between analytes and nanoparticles. A net change in a measured parameter may indicate an accumulated reaction parameter such as the total quantity of analyte bound to nanoparticles. These results can then be used to guide additional measurements to confirm or clear the initial indication. For example, if a sample exhibits a small but suspicious T2 change soon after mixing, the system can initiate a series of tests to determine the rate of change in T2 over a period of time. Then, if those later results confirm that the analyte is present, an alarm can be issued. If the follow-on measurements indicate no analyte, then the initial suspicion may be cleared, thereby averting a false alarm. Using a provisional re-scan protocol, combined with a rate-magnitude analysis, the system enhances both reliability and threshold sensitivity.

Based on experimental results and theoretical modeling, a positive T2 change is due to analyte displacing water molecules upon binding to the nanoparticles, and negative T2 change is due to repeated dephasing of water molecules within a cage structure formed by multiple nanoparticles. In addition, the positive or negative T2 change can be promoted by processing and stoichiometry. For example, the ratios of nanoparticles and the reagent can be adjusted to provide negative or positive T2 changes.

In some circumstances it can be important to measure both negative and positive T2 effects so as to detect analyte despite an interferent present in the sample solution. For example, a test sample contaminated with a paramagnetic ion, such as humic acid with chelated iron, causes a reduction in the T2 of the mixture. If the sample contains an analyte mixed with the humic acid, the analyte can be detected despite the interferent in the following manner. First, measure the sample prior to mixing the nanoparticles, to generate a first T2 measurement value. Then, mix the nanoparticles into the solution and perform a second T2 measurement, completing that measurement before the analyte has had time to interact with the nanoparticles. Then allow the analyte to interact with the nanoparticles, and then measure T2 a third time. The initial measurement reveals the presence of the humic acid interferent so that the resulting T2 effects may be accounted for. The second T2 measurement, in comparison with the first value, provides a check that the nanoparticle concentration and other mixing parameters are correct. The third measurement reveals the analyte as a change in T2 relative to the second measurement, the change being due to the analyte-nanoparticle interactions.

Alternatively, in some circumstances a separate baseline measurement cannot be taken, or it may not be known when the analyte interacts with the nanoparticles. However many interferents, including humic acid, cause a negative shift in T2. In that case the nanoparticles can be mixed so as to generate a positive T2 shift upon binding to the analyte. When the positive T2 shift is larger than the negative shift from the interferent, the analyte may thus be detected.

In one aspect the invention includes nanoparticle multiplexed mixtures which detect any of a plurality of different, but specific, analytes. "Nanoparticle multiplexed mixtures" are nanoparticle preparations sensitized to multiple analytes. There are two multiplexing scenarios. In the first scenario, each nanoparticle in the mixture is sensitized to a single analyte. Nanoparticles sensitized to different analytes are then mixed together in the solution. In the second scenario, each nanoparticle is sensitized to multiple analytes.

In one embodiment, an automated air monitoring system includes inlets to admit an airborne sample along with air, a collector that gathers the sample material and concentrates it into a liquid form, called a raw sample, and a fluidics system. The fluidics system holds the raw sample, for example in a container and provides consistent metering of the raw sample, for example via an outlet tube using a pump such as a peristaltic pump. Metered sample is mixed with selected nanoparticles which may be in water, for example, drawn from reservoirs via an outlet by a pump. As soon as the analyte-nanoparticle reaction takes place the fluidics system moves the sample into the sample area of the magnetic resonance system for measurement, for example, via a tube driven by a pump. Alternatively, sample mixing and processing may take place within the magnetic resonance system. The fluidics system may include means for cell lysing wherein the fluidics system may lyse or disrupt cells or viruses in the sample to release proteins, RNA, or DNA of the target cell. The fluidics system may also have a temperature control built in to speed up the binding event. Fluidics system also may have an overall system cleaning solvent to eliminate contamination. The cleaning solvent or rinsing agent can be drawn from a reservoir and pumped through the tube which delivers the samples to the sample area. The fluidics system also allows positive and negative control tests to ensure the overall system is functional, and performs calibration tests using calibration standards.

In one embodiment, chelates are used in place of nanoparticles to generate the distinct magnetic field region and to bind to analyte. An advantage of using chelated ions is that it allows faster diffusion through the liquid medium to speed up diffusion-limited processes. On the other hand, with nanoparticles one can tailor the affinity molecules to select the analyte desired, whereas chelates occur only in specific molecular forms. Nanoparticles have more area to attach the affinity molecules compared to chelates. As an alternative, nanoparticles can be decorated with chelates for binding to analytes, explosives and chemicals.

In one aspect, the second magnetic field region, being generated by paramagnetic cores or chelates or other magnetic structures, has a size comparable to the size of the analyte, so that the bound analyte just fills the second magnetic field region, excluding the liquid from that region, thus providing highest signal and highest sensitivity. For example, when the analyte is a relatively small molecule such as an explosive vapor molecule or a chemical weapon molecule, then the size of the second magnetic field region is preferably chosen to be in the range of 1 to 10 nm. To detect a larger analyte, such as a toxin or DNA or virus particle, then the size of the second magnetic field region would be 10 to 100 nm. When the analyte is an even larger objects such as a bacterium, the size of the second magnetic field region may be 100 to 1000 nm or larger as needed to match the analyte.

The nanoparticles may include structures that provide an optical signature. For example, fluorescent dyes or centers may be attached to or included within the nanoparticles, and may be exposed to photons of sufficient energy to excite fluorescence, causing emission of fluorescence photons having an energy different from, and usually lower than, the excitation photons. The excitation and fluorescence photons may be in the ultraviolet, visible, or infrared range. Detection of the fluorescence photons provides a measure of the nanoparticle concentration. In addition, the structures may be modified when analyte binds to the nanoparticle, and such action may result in a detectable change in the fluorescence such as a change in the intensity or energy of the fluorescence photons. Detection of this change would provide an indication, independent of magnetic resonance measurements, that analyte binding has occurred and thus that analyte is present in the sample.

Other features and advantages of the invention will be apparent from the following detailed description, the claims and the appended drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Figure 1:
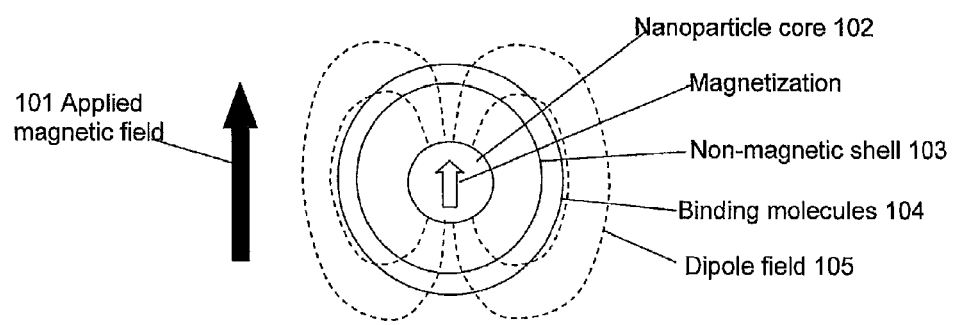
FIG. 1 is a schematic representation of a nanoparticle showing the applied magnetic field and the second magnetic field around the nanoparticle.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Magnetic Resonance

A brief summary of the technical elements used in certain embodiments is provided herein. The analyte or target molecule is contained in a medium, preferably a liquid such as water, which includes an atomic nucleus that has a non-zero spin, such as hydrogen. As is well known, (see for example, Pulse Methods in 1D & 2D Liquid-Phase NMR, Wallace S. Brey, Academic Press 1988), that the magnetic component of such a nucleus becomes polarized or spatially oriented in a magnetic field, and may be induced into magnetic resonance precession at a frequency given by:

$$f_{Larmor} = \gamma B / 2\pi$$

where B is the magnetic field strength at the position of the nucleus, $\gamma$ is the magnetogyric ratio of the nucleus, and $f_{Larmor}$ is the resonance frequency or Larmor frequency ($\gamma = 2.675 \times 10^8$ Tesla$^{-1}$ sec$^{-1}$ for the hydrogen nucleus). The magnetic components, or magnetic moments, of the nuclei are vector quantities and add to give a resultant bulk magnetization vector that is the NMR signal measured by NMR spectrometers.

Following a perturbation such as that employed in recording NMR signals (see below), the bulk magnetization vector recovers to its original steady state over time; this process is referred to as nuclear magnetic relaxation. Two fundamental time constants are used to describe this relaxation in terms of a single-exponential process. Recovery of the bulk magnetization along the direction of the first magnetic field is described by the spin-lattice relaxation time or longitudinal relaxation time, designated as T1. Typically, T1 is of order milliseconds to seconds. The single-exponential decay of bulk magnetization in the plane perpendicular to the direction of the first magnetic field is described by the spin-spin relaxation time, or transverse relaxation time, designated as T2. For liquid signals, T2 is generally in the range of 100 milliseconds or more. Solid samples on the other hand, generally have T2 values in the range of 1 to 100 microseconds.

A magnetic resonance measurement is performed by applying one or more RF (radio frequency) energy pulses to the sample and measuring the bulk magnetization that becomes reoriented by the pulse. The RF pulses have a frequency equal to the Larmor frequency, and duration sufficient to cause the bulk magnetization vector to reorient into a plane perpendicular to the first magnetic field, where the bulk magnetization vector (the NMR signal) can be recorded over time. The RF pulses therefore, are usually multiples of 90 degrees.

Spin-spin relaxation is typically measured by a series of RF pulses to give rise to spin echo signals. A spin echo is generated by a 90-degree pulse followed by a small delay time (typically designated as $\tau$), followed by a 180-degree pulse (90°–$\tau$–180°. A second $\tau$, identical in time to the first, is used before the bulk magnetization vector is recorded. The series of RF pulses and time delays is used to first dephase the nuclear magnetic moments comprising the bulk magnetization in the plane perpendicular to the first magnetic field during the first $\tau$, and refocus the remaining bulk magnetization in this plane during the second $\tau$. This latter refocusing creates an echo signal, which can be recorded. The most common method to measure spin-spin relaxation is that originally described by Carr and Purcell (Carr, H. Y. and Purcell, E. M.: Effects of Diffusion on Free Precession in Nuclear Magnetic Resonance Experiments, Physical Review 94, no. 3 (1954): 630-638), a modification of the method described earlier by Meiboom and Gill (Meiboom, S. and Gill, D.: Modified Spin-Echo Method for Measuring Nuclear Relaxation Times, The Review of Scientific Instruments 29, no. 8 (1958): 688-691). The Carr-Purcell modified Meiboom-Gill (CPMG) method uses a series of small time delays followed by 180-degree pulses after the initial 90°–$\tau$–180° sequence described above. This in turn is followed by the resultant bulk magnetization vector $[90_x°-(\tau-180_y°-\tau-\text{record})_n]$. The amplitudes of the spin echo signals are proportional to the bulk magnetization remaining at the time of the echo, which becomes successively smaller as the number of sequences increases (as the value of n increases). Therefore, measuring the amplitude of the bulk magnetization vector after various values of n and fitting the data to a single exponential decay with T2 as the relaxation time provides a direct measure of T2.

Paramagnetic Nanoparticle Fields

In a preferred embodiment, nanoparticles are employed to influence the magnetic field in a region close to the nanoparticles. The paramagnetic or superparamagnetic core of the nanoparticle becomes magnetized when an external magnetic field is applied to it. Superparamagnetism is related to ferromagnetism in which the size of the magnetized body is too small to form a magnetic domain. The superparamagnetic core exhibits a high permeability and fairly high saturation field comparable to iron, but little or no hysteresis ($H_c \sim 0$). When placed in a magnetic field, the core becomes strongly magnetized parallel to the direction of the applied field. When the external field is removed, the core loses essentially all of its magnetization. Disregarding anisotropy and shape effects, the induced magnetic moment of the core is given by:

$$m_{core}=(4\pi/3)(r_{core}^3)(\chi B_0)$$

where $m_{core}$ is the dipole moment of the core, $r_{core}$ is its radius, $B_0$ is the applied field, and $\chi$ is the susceptibility. Normally $\chi \approx 0$ for nonmagnetic materials, $\chi \gg 1$ for superparamagnetic materials when $B_0$ is below a saturation field, and $1 \leq \chi \leq 0$ for $B_0$ above saturation. For example, magnetite ($Fe_3O_4$) is superparamagnetic with a susceptibility of about 1 for fields below saturation of about 0.5 Tesla.

The magnetized core produces a magnetic field which usually approximates a dipole field, or the magnetic field produced by an ideal magnetic dipole located at the center of the paramagnetic core of the nanoparticle. At locations outside the nanoparticle core, the dipole magnetic field is parameterized as follows:

$$B_r = 2m_{core} \cos \theta / r^3$$

$$B_\theta = -m_{core} \sin \theta / r^3$$

Here $B_r$ is the radial component of the dipole field, $B_\theta$ is the circumferential component, r is the distance from the center of the core, $\theta$ is the polar angle relative to the applied field, and $m_{core}$ is the dipole moment.

The dipole field adds linearly to the applied field (as vectors), resulting in the net magnetic field. The Larmor frequency is determined by the net magnetic field experienced by the polarized nucleus. Components of the dipole field orthogonal to the applied field cause primarily a field rotation, whereas the dipole components parallel to the applied field directly change the magnitude of the net field and therefore change the Larmor frequency, relative to the undistorted applied field. The net field $B_{net}$, disregarding second order terms, and for $r \gg r_{core}$, is as follows:

$$B_{net}=B_0(1+4\pi/3(r_{core}/r)^3 \chi (2 \cos^2 \theta - \sin^2 \theta))$$

In some embodiments the magnitude of the gradient of the net magnetic field is also important. The field gradient is given by:

$$\nabla B_{net}=B_0 \chi 8\pi (r_{core}^3/r^4)(-\{r\} \cos^2 \theta + \{\theta\} \cos \theta \sin \theta)$$

where curly brackets denote unit vectors in the r or $\theta$ directions.

Diffusion in a Liquid

Some embodiments include a liquid medium. The liquid contains the analyte and the nucleus that emits the magnetic resonance signals. Those signals are influenced by diffusion, particularly the diffusion of the molecules of the liquid through the liquid, or molecular self-diffusion. Diffusion is formulated as follows:

$$\sigma_{walk}=(2 D_{molec} t)^{1/2}$$

where $\sigma_{walk}$ is the average distance traveled in an isotropic three-dimensional random walk in time t, and $D_{molec}$ is the translational diffusion coefficient. For example, $D_{molec}=1.5 \times 10^{-9}$ m²/s for water at room temperature.

Magnetic resonance measurements are also influenced by spin diffusion, a phenomenon in which the spin or polarization of a nucleus is interchanged with that of a nearby nucleus of the same type. Spin diffusion can distribute spin-dependent effects, such as depolarization, throughout the sample. For example, if a small fraction of the hydrogen nuclei in water experience a depolarizing force, spin diffusion can cause all of the hydrogen in the sample to assume an averaged polarization value.

A Model

This model addresses spin-dependent interactions between nanoparticles and solvent, and provides a useful framework for quantifying the observed T2 effects. It is used in some embodiments as the basis for measuring and detecting analytes. A simplified nanoparticle is assumed to consist of a spherical core of superparamagnetic material, surrounded by a spherical shell of non-magnetic material, all in water. However, the model can be applied or modified for use with nanoparticles of other shapes and for use with other solvents. The model suggests the following mechanisms for the observed T2 changes:

(1) Nanoparticles in solution reduce T2 relative to plain water. The model suggests that depolarization is due to a dipole magnetic field produced by the magnetized core. The field distortion causes spins to precess at different frequencies, leading to destructive interference. Although CPMG normally refocuses static field-nonuniformity effects, the Brownian motion of the water molecules causes them to enter and exit the field distortions in a time shorter than the echo interval, thereby making the spin dispersion time-dependent and breaking the CPMG refocusing effect.

(2) When nanoparticles react with analyte, but do not agglomerate, the T2 increases. This may be due to the analyte molecules occupying part of the distorted-field region around the nanoparticle, thereby excluding water from that region, thus reducing the spin dispersion and increasing T2. Similarly, when chain or string like structures of nanoparticles and analyte are formed, T2 increases. Formation of the chains is described below in connection with the use of magnetic fields.

(3) T2 decreases when nanoparticles and analyte agglomerate. This may be due to the formation of a water-filled cage-like structure in which water molecules undergo repeated spin-dispersion collisions with the surrounding nanoparticles. Sufficient repetition of incremental depolarization would reduce T2, despite the analyte occluding portions of the non-uniform field regions.

(4) A single exponential usually fits the polarization decay curve. This is despite the fact that hydrogens close to nanoparticles are strongly dephased, while the general solvent sees only a uniform field, a two-population system. However, the spin populations are rapidly equilibrated across the sample by spin diffusion via homonuclear flip-flop interactions, resulting in a single averaged T2.

The model nanoparticle is depicted in cross section in FIG. 1 in the presence of an applied magnetic field indicated by arrow 101. The nanoparticle comprises a magnetizable core 102, a non-magnetic shell 103, and binding molecules 104. The core 102 preferably is paramagnetic and more preferably is superparamagnetic. The induced local dipole-shaped field 105 of the nanoparticle is represented by the dashed lines. The radius of the core 102 should be large enough to produce a significant magnetic field distortion in a large enough region to produce a change in T2 of the liquid in that region. The radius of the core 102 should be small enough that the core 102 does not become ferromagnetic. Typically the core radius is about 1 to 20 nm. Desirable properties of the core 102 include high susceptibility at the applied magnetic field strength, high saturation field preferably in excess of the applied magnetic field strength, chemical compatibility with the liquid medium, and very low remnant field. The last feature is desirable to prevent nanoparticles from clumping together due to magnetic attraction. The core material may be any magnetizable material such as iron oxide, cobalt, and nickel compounds. Nanoparticles can be non-toxic and biodegradable if an iron core is used. The core is coated by one or more shells 103 of non-magnetic material, for example, dextran or silica. Silica coatings are stable and robust, and may avoid the need for refrigeration. Other polymeric coatings may be considered such as polystyrene, polyacrylic acid, polyacrylamide and polyvinyl alcohol.

Figure 2:
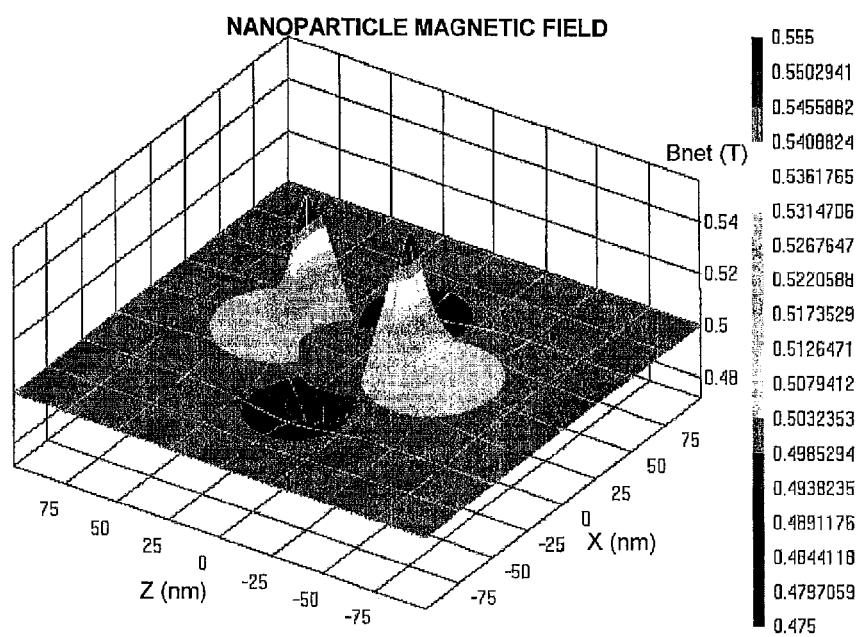
FIG. 2 is a graph of the net magnetic field surrounding the nanoparticle of FIG. 1.

The net field magnitude at location $(r,\theta)$ around the nanoparticle has both positive and negative variations relative to a uniform field. This is shown in the graph of FIG. 2.

While the CPMG procedure refocuses static field nonuniformities, those water molecules that move from one field region to another, in the time between refocusing pulses, are not refocused and produce T2 effects. Thus, T2 changes are related to the gradient of the net field.

To consider a specific example, the core is $Fe_3O_4$, with a 4-8 nm diameter, and the rest of the particle is a dextran shell, with an overall 50 nm diameter. The susceptibility and saturation field depend on the composition, crystal structure, and core diameter. Values of the saturation field range from 0.2 to 0.5 T, and susceptibility ranges from 0.2 to 2. A numerical simulation was prepared using 0.5 T saturation and 0.5 for susceptibility. The net field in the vicinity of this nanoparticle is shown in FIG. 2. Strong field enhancements at the two "poles" of the particle are seen, relative to the field reduction around the "equator". The field within the shell is of no interest and is not calculated; it is plotted as $B_0$.

Figure 3:
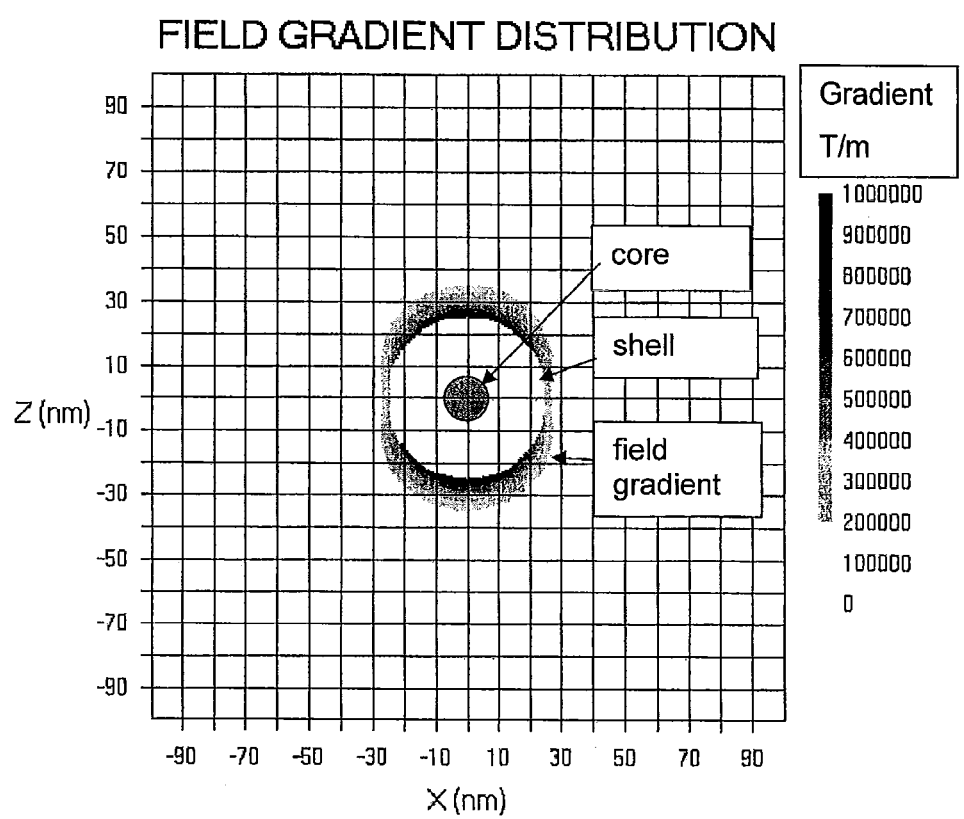
FIG. 3 is a plot of the magnitude of the magnetic field gradient around the nanoparticle.
Figure 4:
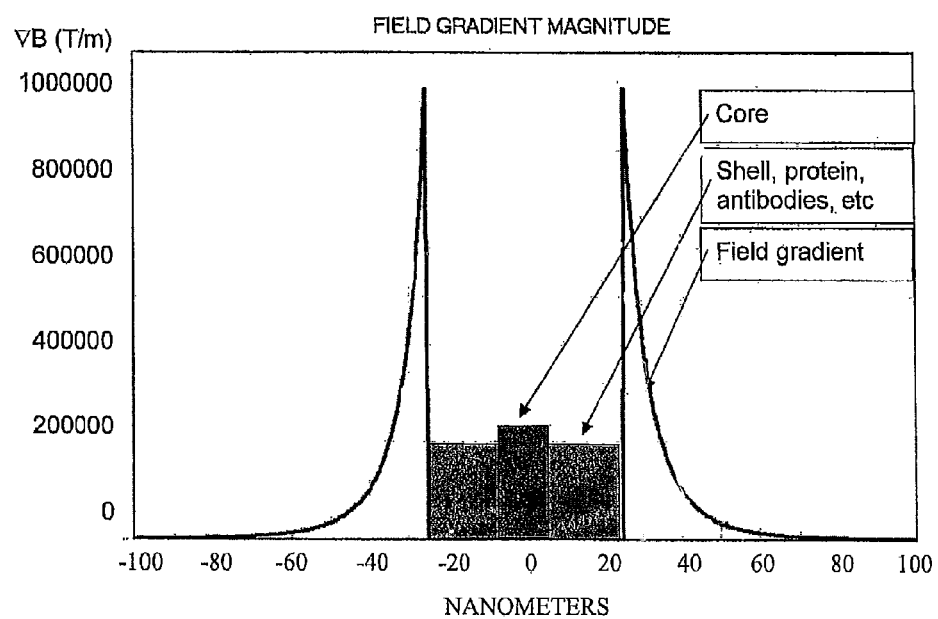
FIG. 4 is a plot of the field gradient magnitude along the axis of the particle.

The magnetic field gradient is shown in FIGS. 3 and 4. FIG. 3 is a plot of the magnitude of the field gradient around the nanoparticle. FIG. 4 is a plot of the field gradient magnitude along the axis of the particle. Again, fields inside the particle are not analyzed.

For an echo interval of $T_{Echo}=4$ msec, the average walk distance is about 3.5 microns. This is much larger than the length scale of the distorted-field regions; hence it is safe to assume that the water molecule has enough time to enter and exit the distorted-field region between refocusing pulses.

The spin dephasing produced by the water molecule passing through the distorted field region can be estimated as follows. The instantaneous precession frequency is proportional to the net magnetic field at the water molecule's location. For simplicity we assume that the molecule random-walks through the distorted-field region of one nanoparticle, during one echo interval, starting and ending in the solvent exterior to the distorted-field region. Thus the molecule trajectory begins and ends in the applied field of $B_0$ but passes through the distorted-field region between CPMG echoes. While the molecule is within the distorted field, it accumulates extra precession compared to molecules in the rest of the solvent. That portion of the phase advance due to the $B_0$ field is then refocused as usual by the 180 pulses, but the extra precession phase, accumulated during the time spent in the distorted field, will not be refocused. The unrefocused phase increment due to traversal of a field distortion is the integral of the field experienced by the particle, minus that in the applied field alone:

$$d_{phase} = \int \gamma(B_{net}(r) - B_0) dt$$

where $d_{phase}$ is the accumulated phase difference between a hydrogen which passes through $B_{net}$ (here an explicit function of space) versus one remaining in the uniform field $B_0$, $\gamma$ is again the Larmor coefficient and the integral is over the time between refocusing pulses. To obtain a rough estimate of the phase shift, the previous equation may be simplified by assuming that the molecule resides in a constant field for a time needed to diffuse through the distorted field region, resulting in the following approximation:

$$d_{phase} = [x_{dis}^2/(2D_{molec})][B_{net} - B_0]\gamma$$

Using the nanoparticle sizes and field assumptions discussed above, the net magnetic field deviates from the applied field by typically 20 mT. The spins within that field will precess about 850 kHz faster than in the undistorted field. A typical length scale for this distortion is $x_{dis}=20$ nm. The time needed to diffuse 20 nm is 133 nsec. During that time, the spins precess an extra $d_{phase}=0.1$ radians. This represents a substantial dephasing in a single echo interval by a single molecular traversal, which if not refocused by CPMG will result in a short T2. In the sample, many water molecules will be interacting with the nonuniform field continuously, and each will experience a positive or negative phase shift depending on the specific path. In the ensemble, the extra spin dispersion causes destructive interference and overall depolarization. The spin diffusion coefficient in water is in the range of $D_{spin} \approx 10^{-15}$ to $10^{-16}$ m$^2$/s, depending on temperature and other factors. Although spin diffusion is slower than molecular diffusion, it is sufficient to spread the depolarization among many water molecules in a few msec. Interestingly, solid-state spin diffusion rates tend to be much higher, of order $10^{-9}$ m$^2$/s which is comparable to the molecular diffusion in free water. If the shell exhibits rapid spin diffusion, it could serve as a conduit for distributing polarization among all of the water molecules contacting the nanoparticle surface.

Several experiments have demonstrated a T2 increase of 20 to 200 msec. The model suggests that this is due to the analyte molecules obstructing the surface of the nanoparticle, effectively preventing water molecules from sampling the distorted-field regions at the surface of the nanoparticle.

When analyte molecules attach to the surface of a nanoparticle, a portion of the surface is occluded. The global depolarization rate goes down and T2 increases. The change in decay rate is roughly proportional to the fraction of the distorted-field volume occupied by the analyte. If multiple analyte molecules are attached, they all contribute a similar T2 change on average. If the analyte spends only part of its time covering up the surface of the nanoparticle, then the T2 change scales proportionately.

A decrease in T2 may also be observed by changing the ratio of the nanoparticles to antibodies. Here antibody is used as an example of the connection to the analyte. This is defined as stoichiometry control. Depending on the level of detection of analyte one can adjust the stoichiometry to allow rapid detection of analyte.

The reagents and processing conditions may be adjusted to cause a decrease in T2. Formation of extended aggregates of nanoparticles and analytes is correlated with such a T2 decrease. The model posits that the aggregates are open, cage-like structures through which water molecules may pass easily. This is not explained in earlier studies. In one embodiment, spin information diffuses in and out of the agglomerate structure rapidly, so that the depolarization occurring within the cage is equilibrated throughout the sample.

The model suggests that the T2 decrease for agglomerates is due to repeated dephasing when water molecules within the cage repeatedly encounter depolarizing fields. Such repeated dephasing represents a more effective polarization sink than isolated nanoparticles in the free liquid because the caged water molecule remains in close proximity to numerous nanoparticle surfaces. While portions of the nanoparticle's distorted-field volumes are occluded by analyte, the water molecule could spend a significant fraction of its time sampling fields that differ from the main field, and thus would become totally dephased in a time short compared to the echo interval. Then, by trading polarization with neighboring molecules including those outside the agglomerate, a uniformly reduced T2 would result.

The model has utility because it leads to new measurements and new ways of performing measurements related to analyte in the sample. The model explains how the analyte interactions with nanoparticles produce both increases and decreases in T2, and suggests ways to control the effects by adjusting reagent concentrations. Noting that speed of detection is a critical parameter for many applications, the model suggests that the T2 increase method due to analyte-nanoparticle binding will provide the signals faster than the T2 decrease from aggregation, because binding must occur before the agglomerations. The model also guides the development of more sensitive nanoparticles using higher-susceptibility core material and thinner non-magnetic shells. The model also leads to steps for canceling systematic errors, such as measuring the T2 of the nanoparticle solution and the sample separately, before mixing, to better quantify any T2 changes from the binding. The model also explains how thermal effects and diffusion effects participate, and can be exploited to accelerate the detection or confirm analyte reactions. The model also guides the development of products exploiting the inventive methods by quantifying signal and noise versus sample size and other design parameters.

Method Description

In one embodiment a method for detecting one or more analytes includes: preparing a liquid sample mixture, which may contain the analyte and other materials; applying a first magnetic field to the liquid; preparing a second and distinct magnetic field within a special region of the liquid; maintaining the analyte, if any is present, within the special region (for example, by providing means for holding the analyte, securing that binding agent adjacent to the special region and allowing the analyte to interact with the binding agent); exciting magnetic resonance signals from the mixture while the analyte is maintained within the special region; analyzing the signals to determine whether analyte occupies the special region; and then concluding that analyte is present when the signals indicate that the liquid is displaced from the special region. In one embodiment nanoparticles having a binding agent for the analyte of interest are used to create the special region and to hold analyte within the special region.

In one embodiment preparing the liquid sample mixture includes the use of a liquid which contains an atom with a nucleus having non-zero spin. The atoms may be an intrinsic part of the liquid, or they may be added as solute. The step of preparing a liquid sample can include mixing or stirring to ensure that analyte reaches the nanoparticles. Mixing can be achieved in numerous ways, including by driving the sample fluids through convoluted tubes using a pump, and such motion may be unidirectional or reciprocal to produce the desired level of mixing. Alternatively, the nanoparticles and the analyte may be contained in the same type of liquid, so that when the nanoparticles and analyte are placed in the same container, they spontaneously become mixed without the need for physical stirring. For example, the nanoparticles and the sample material may be dissolved in water and then intermingled by diffusion in the measurement container. Unassisted mixing may also be arranged by use of highly miscible solvents, such as alcohol and water, for the various ingredients.

The method can also include using a magnetic field to enhance the reactions between the nanoparticles and the analyte. The magnetic field to enhance reactions may be the same field as that used for magnetic resonance measurements, or the two magnetic fields may be different. In one embodiment the steps of a method for enhancing reactions between the nanoparticles and the analyte are: (1) place the analyte and nanoparticles in a fluid medium and allow the nanoparticles to bind to the analyte to form complexes; (2) apply a magnetic field to the complexes, thereby magnetizing the nanoparticles; (3) then allow the magnetic field to exert forces on the nanoparticles and allow the magnetized nanoparticles to exert magnetic forces on each other; and (4) allow the complexes to move responsive to those forces. For example, if the applied magnetic field is non-uniform, the complexes are drawn into a region where the magnetic field is strongest, and are concentrated in that region. The interactions are then accelerated due to the increased concentration of the complexes.

In different embodiments, steps (1), (2), and (3) occur in various orders and simultaneously. The nanoparticles and analyte may first be placed in a fluid medium and then bind with the analyte to form complexes, or the complexes may be formed elsewhere and then added to the fluid medium. The attachment of the reactants to nanoparticles can be any association sufficiently strong so that the reactant can be carried along with the nanoparticle when the nanoparticle moves through the fluid medium under influence of magnetic forces. The magnetic field may be applied before or after the analyte binds to the nanoparticles. This method can also be combined with the described mixing and/or temperature cycling.

The magnetic field to enhance reactions may be substantially uniform or a highly non-uniform field, and may have a particular shape or direction, and may be generated by external means, and may be generated or shaped in cooperation with the reactants or the nanoparticles or paramagnetic beads other magnetic entities. The magnetic field to enhance reactions may be generated by electromagnets, permanent magnets, superconducting magnets, or any source of magnetic field. The strength of the magnetic field is sufficient to magnetize the nanoparticles, which usually falls in the range of about 0.01 to 20 Tesla. The field may be on all the time, as with a permanent magnet, or it may be transient, as with a pulsed electromagnet. Magnetization of the nanoparticles is essentially instantaneous when they enter the magnetic field.

The magnetic field is produced by a magnet, which may be an electromagnet, a permanent magnet, a superconducting magnet, or any other source of magnetic field. The preferred magnet type depends on the sample size. For small sample volumes of order 1 milliliter or less, permanent magnets are preferred because they require no electrical power, do not generate ohmic heat, and do not require a cryostat. A wide variety of strong permanent magnet forms are available, including NdFeB (neodymium iron boron) which forms provide a strength (field-energy product) of 30 to 55 MGOe at moderate cost. When mounted in a suitable magnetic circuit, these permanent magnets are capable of generating fields exceeding the saturation field of ferrite, which is the paramagnetic component in many nanoparticles, and of producing strong field gradients of 1 Tesla/cm or higher. Such fields and field gradients are sufficient for many magnetic separation applications including concentration of nanoparticles, magnetizing paramagnetic beads, and chain formation.

In step (3), the magnetic field to enhance reactions exerts forces on the nanoparticles when it is non-uniform, and urges them in the direction of increasing field strength. The nanoparticles exert forces on each other, urging neighboring nanoparticles into alignment with the applied magnetic field, drawing them together when so aligned, and repelling them when positioned perpendicular to the field. The various forces occur continuously and essentially instantaneously.

In step (4) The analyte and nanoparticles move in the same way because they are sufficiently strongly attached, that the magnetic forces do not detach the analyte. Often the net motion is to bring the analytes closer together, thereby promoting interactions between them. That is the case when the applied field is non-uniform, thus concentrating the complexes into the strongest field region. For example if the non-uniform magnetic field draws the complexes into a sub-volume comprising one tenth of the volume of the initial mixture, then the average distance between reactants is reduced by a factor of 2.16 which, for diffusion-limited processes, increases the reaction rate by a factor of 4.7. The net effect of mutual magnetic forces between nanoparticles is also primarily to cause complexes to come together, when the complexes are free to move, because those forces first realign the complexes with the field, and then draw them together.

Figure 5:
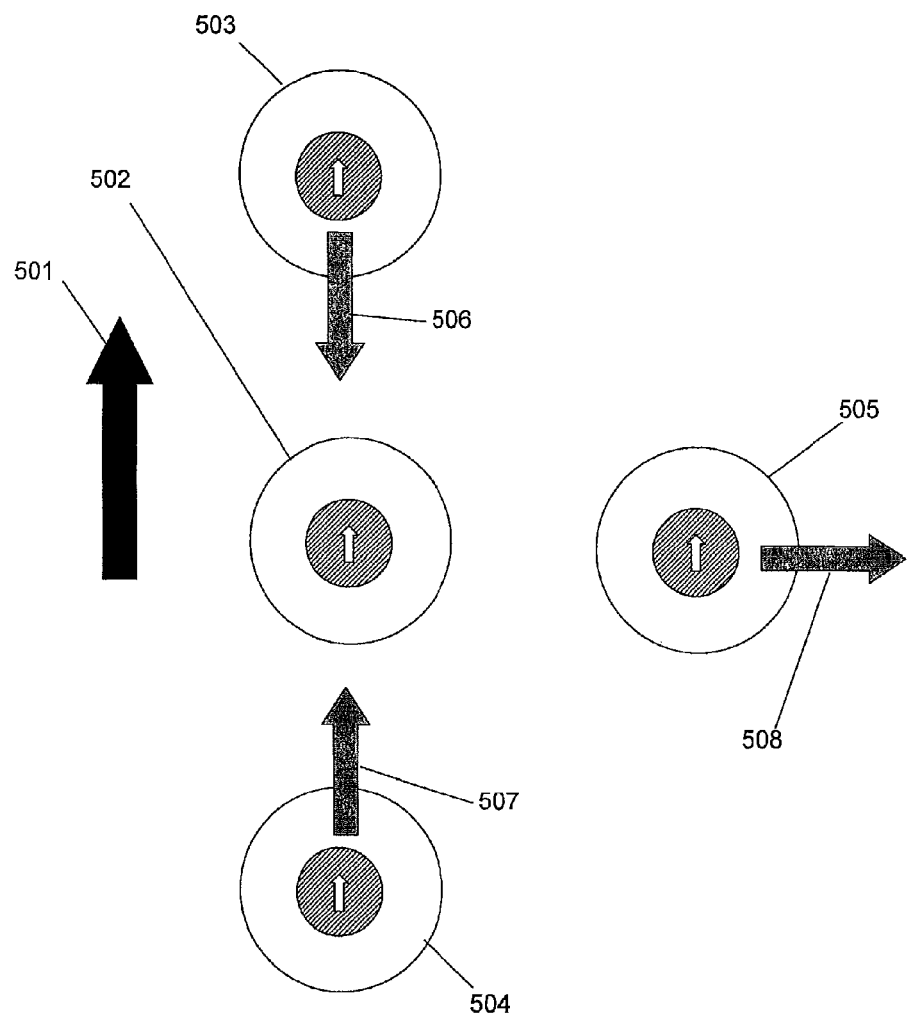
FIG. 5 is a schematic representation of the mutual forces between nanoparticles in a magnetic field.

Alternatively, the magnetic field of steps (3) and (4) may be substantially uniform. The nanoparticles exert mutual magnetic forces on each other, due to the dipole-shaped magnetic fields generated by the magnetized cores of the nanoparticles. These dipole-dipole forces cause the nanoparticles to move in various ways, and the motions influence the interactions of the nanoparticles and of the attached analytes. The forces between magnetized nanoparticles are illustrated in FIG. 5. The direction of the applied magnetic field to enhance reactions is given by the arrow 501. A particular nanoparticle 502, and neighboring nanoparticles 503, 504, and 505 are shown. All of the nanoparticles in FIG. 5 are magnetized in the same direction, as indicated by the small white arrows. The nanoparticles 502 and 503 are aligned with the applied field, and thus attract each other. The force exerted on nanoparticle 503 by nanoparticle 502 is shown by a gray arrow 506, which points toward nanoparticle 502 signifying that nanoparticle 503 is attracted toward nanoparticle 502. An equal an opposite force exerts on nanoparticle 502, but for graphical clarity is not shown.

Also in FIG. 5, another nanoparticle 504 is in parallel alignment with 502 but on the other side of nanoparticle 502. Nanoparticle 504 is also attracted toward 502 as shown by arrow 507.

Nanoparticle 505 is perpendicularly oriented relative to 502 and the field. Correspondingly, the dipole-dipole force exerted on 505 is repulsive, as shown by arrow 508. Not shown are additional forces which the peripheral nanoparticles 503, 504, and 505 exert on each other. In an actual mixture, all of the nanoparticles exert forces on each other continuously.

Dipole-dipole forces tend to produce linear chain-like structures. As an example, the nanoparticles can include a bonding means represented as A with the nanoparticle represented as N. The bonding means represented by A may be polyclonal, or able to bond to multiple nanoparticles. Accordingly, in step (1) the reactants bond to nanoparticles forming complexes symbolized as A-N. Then the interactions of step (4) may produce structures of the form N-A-A-N when the reactants bond as identical partners, or of the form N-A-N-A when the reactants bond to a nanoparticle. Further complexes may be added to form long chains under either scenario. Alternatively, two different bonding means of type A (a 3' probe) and C (a 5' probe) may be attached to the same nanoparticle. Then the complexes are of the form C-N-A-B, and the chains are then of the form C-N-A-B-C-N-A-B-C-N-A-B-C-N.

Figure 6:
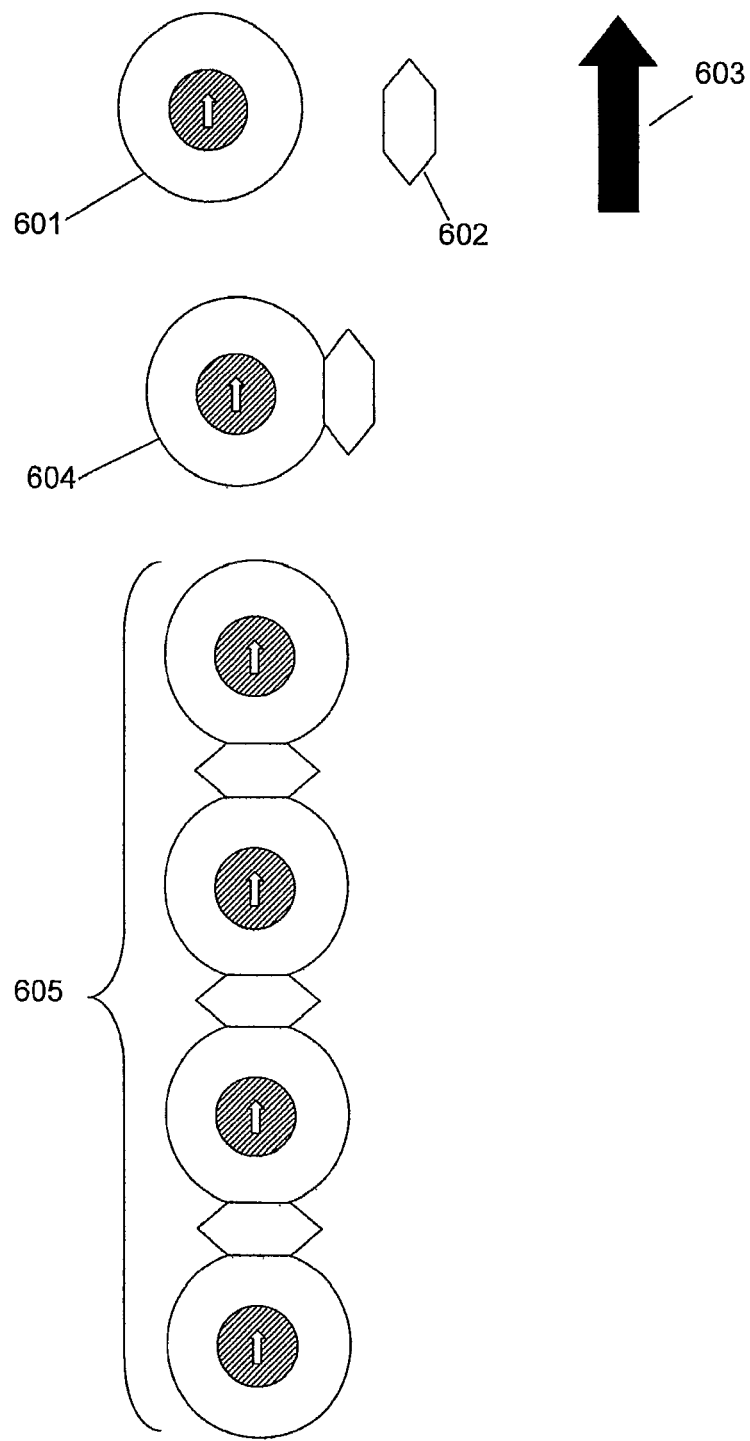
FIG. 6 is a schematic representation of the formation of a chain structure from nanoparticles and analyte.

FIG. 6 is a schematic representation of the formation of a chain structure from nanoparticles and analyte. The example chain structure depicted in FIG. 6 can be formed using the methods and systems described above with a uniform or non-uniform field. The type of chain formation formed depends on the type of nanoparticle employed. A nanoparticle 601 and an analyte 602 are in a magnetic field with a direction indicated by arrow 603. The nanoparticle 601 is of the type that can attach to multiple reactants, that is, for example, a polyclonal nanoparticle. The analyte 602 is of the type that can form bonds to multiple nanoparticles. An example is protein G which can attach to two nanoparticles treated to receive such reactants. In step (1) the nanoparticle 601 and reactant 602 are attached, for example by mixing protein G with suitable nanoparticles in water and incubating them for 4 hours at 37 C. This produces a nanoparticle-reactant complex 604. Multiple such complexes come together in the magnetic field 603 and form a chain 605 of the general type N-A-N-A-N-A-N etc.

The method can also include temperature cycling wherein a sample may be heated or cooled at a fixed location, or the sample may be moved between locations maintained at high or low temperatures. The method can include taking measurements before, during, and after such temperature changes. For example, a measurement for T2 may be taken immediately upon mixing the sample, and again after a period of heating and cooling when the sample comes to equilibrium temperature. Comparison of the T2 values before and after thermal processing will reveal reactions, such as analyte binding to nanoparticles, which occurred during thermal processing.

The method can include the steps of changing the temperature of the sample and then measuring the T2 parameter. Temperature affects the nanoparticle interactions and the magnetic resonance measurement. Selective binding between the analyte and the affinity molecules on the nanoparticles may be accelerated by raising the temperature, particularly for diffusion-limited reactions. Thus the method may include measuring the T2 of a mixture of nanoparticles and unknowns within the liquid at a first temperature, preferably a sufficiently low temperature that the analyte has not reacted with the nanoparticles when the measurement is made. The method may then include the step of heating the sample to a second temperature sufficient to promote analyte-nanoparticle interactions. The method may include measuring the T2 at the second temperature to observe effects of the binding. The method may include a further temperature change, such as return to the first temperature, and further T2 measurements to confirm that the T2 of the sample after the various temperature changes differs from the T2 of the sample before the temperature changes. The steps provide many advantages, including improved discrimination against interferents, demonstration that the T2 change is due to analyte-specific binding, and a check for instrumental errors.

The method may include heating the sample to a temperature sufficient to disrupt the analyte-nanoparticle aggregations, thus producing a solution of analyte-nanoparticle binaries, with a corresponding T2 change. The temperature may be raised further until the analyte is disbonded from the nanoparticles, thus releasing analyte back into the solution and causing a further T2 change. The temperature may then be lowered until binding or aggregation is restored, with corresponding reversion of T2 to the earlier value. This behavior in T2 versus temperature would strongly discriminate against interferents or instrumental errors, and would confirm the presence of analyte.

The method may include the step of measuring the T2 of the sample material prior to mixing with nanoparticles. This would reveal a sample material which causes a shift in T2, such as a high-viscosity solution or chelated iron in the sample. When the sample material causes only a small T2 shift, the measurement may proceed as usual, but in analysis the T2 of the processed sample may be compared to that initially observed in the raw sample to determine whether analyte is present. When the sample produces a large T2 shift, it may be advantageous to dilute the sample until its effects are low enough to permit the magnetic resonance measurements. Analyte in the diluted sample may then be detected as described. When the sample produces such a large T2 shift that magnetic resonance measurements are prohibited, the invention can flag that sample as un-testable, thereby avoiding a false alarm, or it can archive the sample for further analysis.

The method can include preparing a magnetic field in a particular way. The field may be prepared by first generating a substantially uniform first magnetic field with sufficient intensity to permit magnetic resonance measurements, and then perturbing that field locally to produce a second magnetic field, distinct from the first, within a special region. The second field is distinct from the first when the magnetic resonance signals of the liquid outside the special region are influenced by or can be distinguished from signals of liquid inside the special region. For example, the second field can be created by mixing or dissolving paramagnetic particles, for example, those nanoparticles described above, in the liquid. The nanoparticles then spontaneously generate the second magnetic field, in a region closely exterior to the nanoparticles, as a result of magnetization of the nanoparticles by the first magnetic filed. Alternatively, paramagnetic ions such as chelated iron or gadolinium could be employed instead of nanoparticles. An advantage of this approach is that diffusion-limited reaction rates may be increased due to the higher mobility of metal-ion chelates. Similar ions are used in MRI imaging (Gd-DTPA and Gd-DOTA.).

Holding the analyte within the special region can be accomplished by reacting or binding or otherwise attracting the analyte to a material surface or molecule for which the analyte has particular affinity. Such holding may be accomplished by hydrogen bonds, ionic forces, covalent bonds, van der Waals forces, electrostatic forces, or any other type of molecular or material attachment. For example, the holding mechanism may be an antibody raised against an analyte protein, or DNA complementary to analyte DNA sequences, and can include any material surface or molecule for which the analyte has an affinity. Preferably the holding mechanism also has null affinity or negative affinity for all solutes other than the analyte which may be present. Preferably, the holding mechanism is secured proximate to the special region, so that the analyte will be held within the special region. For example, when the special region is exterior to a nanoparticle, antibodies to the analyte, or the other holding mechanisms mentioned above, may be attached to the surface of the nanoparticle, so that the analyte will be held adjacent to the nanoparticle within that region and the liquid will be excluded. Optionally, the nanoparticle may include multiple antibodies, or complimentary DNA, or other binding agents so as to interact with a number of different, but selected, analytes. For example, the nanoparticle could be adorned with complementary DNA for anthrax, antibodies for ricin, and complementary DNA sequences for smallpox, thereby enabling detection of any of these analytes in a single mixture.

The magnetic resonance measurements and analysis to determine whether the analyte occupies the special region can include analyzing the magnetic resonance signals by spectral analysis to seek a frequency component characteristic of the special region. That frequency component, if present, indicates that the liquid is in the special region, and therefore the analyte is not present. Alternatively the step could include applying the CPMG procedure, and analyzing the signals to determine the T2 of the liquid. The T2 distribution may be a single exponential component, or it may include a multitude of components, depending on the spin diffusion rate. In either case, however, a T2 which is longer than the T2 of the baseline case (liquid with the nanoparticles and no analyte) indicates the presence of the analyte.

A variation of the method includes forming an aggregate comprising a plurality of analyte entities. Then, a reduction in T2 (compared to the baseline) indicates the presence of the analyte. For example, an aggregate of nanoparticles with attachment mechanisms and analyte molecules may form when both nanoparticles and analyte molecules have multiple attachment points. Since the aggregation results in a decrease in T2, whereas binding of analyte to nanoparticles results in an increase in T2, it is important to previously calibrate the signals, so that the expected sign of T2 change is known in advance. Nanoparticle stoichiometry can be adjusted to prevent agglomeration or to cause agglomeration depending on the measurement process to be used.

In one embodiment, analyte causes nanoparticles to form extended aggregates. Membrane filters are used to separate those aggregates from the liquid medium. The pore size of the filter is preferably larger than the size of the nanoparticles or of the analyte, but smaller than the aggregates. When an agglomerated sample is filtered, the filtrate has a reduced concentration of both nanoparticles and analyte, which are thus both greatly concentrated as a filter cake. When secondary analysis means are desired, for example to confirm detection of a microbe, the filter cake is used for that secondary analysis. Likewise, the filtrate liquid may be re-measured using the inventive system as an additional check, since the T2 of the filtrate should be much longer than of the initial nanoparticle solution when most of the nanoparticles have been filtered out.

The method may include the steps of measuring the T2 value of a standard. Here a standard is any material which has a known T2. Preferably the T2 of the standard is unchanging in time and is known from prior calibration measurements. For example the standard may be a solution of nanoparticles or of copper sulfate with a concentration adjusted to provide a particular value of T2. Standards enable detection and correction of instrumentation drifts. The standard may be a liquid which is not a solution, such as an oil selected to have a T2 in the desired range. The standard may be arranged to have a T2 substantially equal to that of an analyte-free sample, in which case it is called a negative comparator. The standard may have a T2 close to that produced by the analyte, a positive comparator. The method may include measuring the T2 of multiple standards with different T2 values.

The method can include the step of testing a positive and/or a negative control. A positive control can be a benign analyte, such as bacillus subtilis along with nanoparticles sensitized to it. The positive control may be analyzed at any time, and should be detected in the same way as a threat analyte. Preferably the T2 change produced by the positive control is known from prior calibration, and testing the positive control should always produce the expected T2 change, and failure to do so would reveal a malfunction in the system. A negative control is a benign analyte along with nanoparticles sensitized to some other materials, for example bacillus subtilis combined with nanoparticles sensitized to anthrax. The negative control should never produce a T2 change because the analyte and the nanoparticles are not matched. If a negative control produces a T2 change, it would reveal a malfunction of the system. An advantage of running positive and negative controls is that the entire sample collection, fluidics, sample processing, and detection stages are tested realistically. For comparison, the positive and negative comparator standards discussed in the previous paragraph test only the magnetic resonance portion of the system, not the sample processing stages.

The method can include the steps of producing both an increase and a decrease in T2 of the sample. The increase or decrease in T2 depends on the properties of the nanoparticles, ratios of other reagents such as antibodies, and on other processing parameters. Thus a sample may be tested for a T2 increase using processing steps to generate a T2 increase when analyte is present, and then the same sample may be tested for a T2 decrease by adding the ingredients or processing steps which produce a T2 decrease. Observation of both increasing and decreasing T2 values would enhance the reliability of the analysis and reduce the false alarm rate. Alternatively, two aliquots drawn from the same sample may be processed to generate a T2 increase in one and a decrease in the other.

Interferents are materials which, if present in a sample, cause a change in T2 mimicking that of the target analyte. Most interferents produce a shorter T2, including materials containing chelated iron and materials causing an increase in viscosity of the liquid. Thus the effects of analyte and interferents may be discriminated by processing the sample so that the analyte will produce a T2 increase. For even greater analyte-interferent discrimination, both increases and decreases in T2 may be arranged, either by sequential processing of the same sample or by comparison of parallel aliquots.

The method can include the step of measuring the T2 of a nanoparticle mixture prior to adding the sample material to that mixture. The advantage of this step is that any errors in the nanoparticle concentration or properties would be revealed before the sample material is used. If the nanoparticle solution exhibits an unexpected value of T2 (for example due to a high or low nanoparticle concentration from a metering error) then the nanoparticle solution may be dumped and a new nanoparticle solution may be prepared. If the nanoparticle solution exhibits a value of T2 close to that expected, then the nanoparticle solution may be employed. Preferably the measured value of T2 is then used in the analysis for comparison against the T2 of the mixed and reacted sample, thereby negating errors due to nanoparticle concentration and also improving reproducibility.

The method may include the steps of mixing the sample material and nanoparticles in the liquid, then measuring the T2 of the mixture, then promoting reactions between analyte and nanoparticles, and then measuring the T2 after such reactions. For example, the sample may be shaken or heated to promote the reactions. Simultaneous mixing and heating may be used to accelerate reactions. Comparison of the T2 of the mixture before and after the reactions reveals the analyte. An advantage of these steps is that any errors in the volumes of sample and nanoparticles would be detected and negated.

In one embodiment hazardous chemicals are generally not required. For example, analytes can be tested using only water, salts, nanoparticles, and harmless proteinaceous reagents such as antibodies.

System Description

Figure 7:
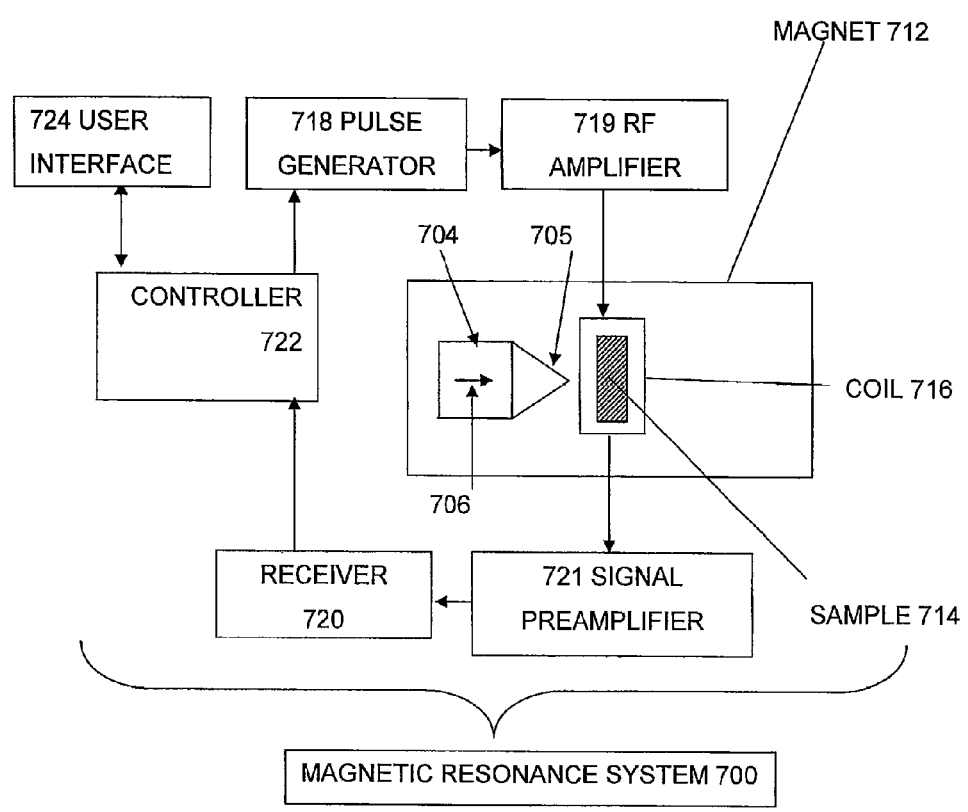
FIG. 7 is a functional block diagram of a magnetic resonance system.
Figure 8:
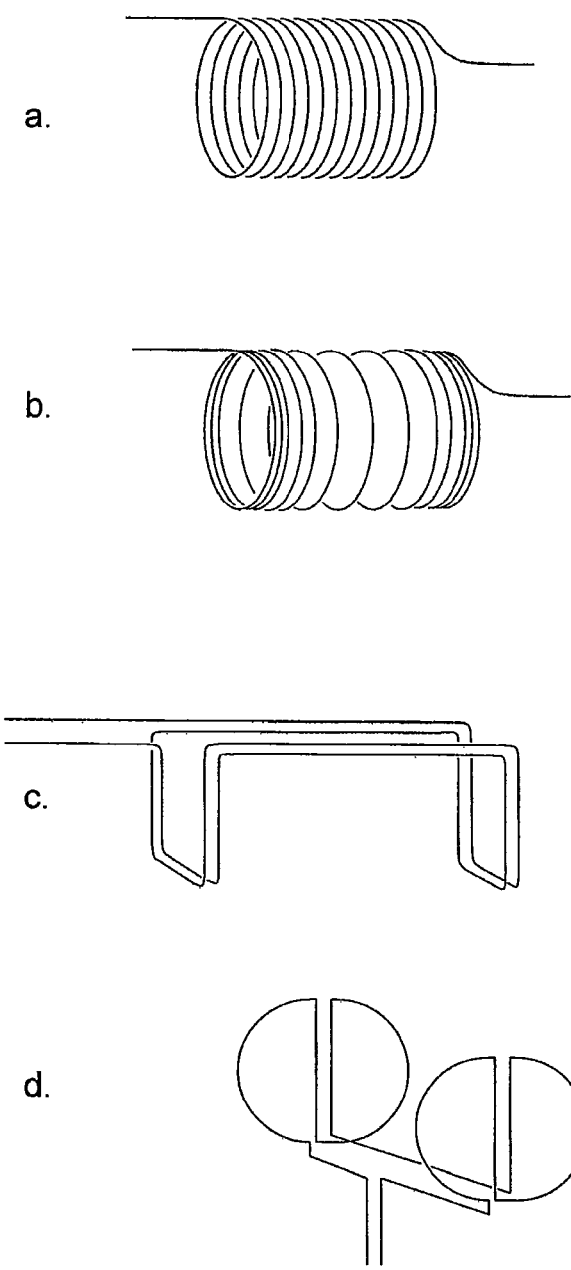
FIGS. 8a-d is a representation of four configurations of the antenna.

One embodiment of a system which can carry out or implement the measurement or detection techniques described above will now be described with reference to FIG. 7 which is a functional block diagram of a magnetic resonance system generally indicated as 700. The system includes magnet or magnet system 712. In one embodiment the magnet 712 is a permanent magnet configured to produce a 0.5 Tesla magnetic field with 0.01% uniformity within a sample area or volume 714 of 1 ml. Alternatively, the magnet system may include an electromagnet, a superconducting coil, or any other source of magnetic field. A coil or antenna 716 is located adjacent to the sample volume. In one embodiment the coil encircles the sample volume 714. A pulse generator 718 is coupled to the coil 716 to provide electromagnetic pulses at the desired Larmor frequency to the sample volume 714. An amplifier 719 may be placed between the pulse generator and the antenna to amplify the signal from the pulse generator. A receiver 720 is also coupled to the coil 716 so as to receive signals picked up by the coil. A preamplifier 721 may be placed between the receiver and the antenna to amplify the antenna signals. The receiver 720 converts the received signals into a digital form. A controller 722 is in communication with the pulse generator 718 and the receiver 720. The controller controls the operation of receiver and the pulse generator. The controller also receives the signals received by the receiver after they have been converted into the digital form.

The controller 722 can be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. Alternatively, the functions of the controller, pulse generator, receiver, and user interface may be combined into a single unit such as an ASIC or FPGA, or a board integrating such circuits. A user interface system 724 is coupled with the controller 722. The user interface system 724 provides a mechanism for interaction between a user and the system 700. The interface system can include, for example, a display such as a liquid crystal screen, indicator lights, a key board, a mouse, an audio speaker, a microphone, switches, or a touch screen.

In an alternative embodiment, a concentrating magnet 704 is provided which includes a field-concentrating pole piece 705 made of, for example, steel. The magnet 704 can be a permanent NdFeB magnet and is magnetized as indicated by the white arrow 706. The magnet 704 and pole piece 705 produce a magnetic field passing through the sample volume 714. The shape of the pole piece 705 is selected so that the magnetic field is highly non-uniform and produces a strong gradient throughout the sample volume 714. The region where the magnetic field is strongest in the sample volume is in the region closest to the pole piece 705. The concentrating magnet 704 can be mounted within the magnet 712 or can comprise a portion of the magnet 712. For example, the magnet 712 can produce a uniform magnetic field in a first region, and a nonuniform field in a second region. Then the sample may be moved between regions of the magnet 712 to perform different tasks. For example the sample may be moved so as to concentrate reactants using the nonuniform field region, and then moved to the uniform field region for measurements.

Alternatively, the concentrating magnet can be located away from the magnet 712. In that embodiment, the sample can be exposed to the field of the concentrating magnet, and can then be placed in the coil 716.

In one embodiment, the field gradient produced by the concentrating magnet acts on the magnetization of the complexes (analyte plus nanoparticle) to draw them into a sub-volume of the sample volume. In that sub-volume, the local concentration of complexes is increased, and continues to increase as further complexes continue to arrive from the rest of the sample. For reactions which are limited by diffusion of the reactants, increasing the concentration of the reactants reduces the average diffusion distance between reactant partners and accelerates the reaction rate correspondingly. For reactions limited by a reaction barrier, the reaction rate is enhanced due to attractive magnetic forces between the complexes.

The RF coil can be made small enough to interrogate volumes of micro liter size. The coil can be made large enough to accommodate liters of sample. FIGS. 8*a-d* are a representation of four configurations of the antenna, each in perspective view. In part a of the figure, a solenoidal coil is shown having a density of windings which is constant along the length of the coil. The sample is placed inside the coil for measurement. The coil acts as an antenna to couple RF energy into the sample nuclei, and also to couple the magnetic resonance signal from the nuclei out to the rest of the system.

In part b of the figure, a solenoidal coil having a variable winding density is shown. The winding densities are higher at the ends of the coil than at the middle. An advantage of using a variable winding density is that the RF magnetic field generated by the coil may be made more uniform than that of a coil of the same size with constant winding density.

In part c of the figure, a two-turn single-sided coil is shown. An advantage of this configuration is that an elongated container such as a tube may be inserted and removed without disconnecting either the coil or the tube.

In part d of the figure, a coil configuration is shown wherein four loops cooperatively generate a transverse RF magnetic field. Elongated samples may be inserted without disconnecting the coil or the tube.

The specific user interface and output of the system are highly application-dependent, but will typically include transmission of information dependent on detection of analyte. For example, such communication may involve recording or archiving test results, displaying a threat alert message, illuminating an alarm or beacon, or activating an acoustical alarm. Communicating data also includes sending signals to other devices, such as automatically shutting off an HVAC system or sequestering a test sample responsive to detection of selected analytes. The communication via the user interface can include electronic, optical, infrared, radio, microwave, mechanical, or acoustical means, or any other means for transmitting data or commands responsive to analyte test results. Additionally, the user interface can include remote communication interfaces such as a network interface card and a wireless access card which are in communication with the controller. These can allow an operator or another device to communicate with the system, to relay commands or retrieve data or convey an alarm. The communication may include transmitting information by the internet, by a local network, or by direct electronic or wireless link.

In one embodiment, the system is configured in two separate chassis, one with the magnet 712, the pulse generator 718 and the receiver 720. The other chassis has the controller 722 and the user interface 724. The two chassis exchange information such as commands and data by an electronic communication link, for example, cables, a wireless link, or a fiber optic link. In a preferred embodiment, the communication link comprises a USB interface employing standard USB connections on each chassis.

The magnetic resonance system 700 can excite magnetic resonance signals from the hydrogen nuclei in water in the sample volume 714 by applying electromagnetic pulses, for example radio frequency (RF) pulses, generated by the pulse generator 718 via the coil. The system detects the magnetic resonance signals from the hydrogen nuclei in the water by inductively picking up the signals in the coil 716. The receiver processes the received signals using amplifiers, mixers, and analog-to-digital converters.

In one embodiment the system 700 measures the T2 of the water by the CPMG procedure or technique under the control of the controller 722. The measurement includes a 90-degree RF pulse generated by the pulse generator followed by a 2 msec delay, and then a string of 2000 180-degree pulses at 4 msec intervals. The phase of the 180-degree pulses is orthogonal to that of the 90-degree pulse. The procedure generates spin echoes in the 4 msec intervals which are received by the receiver 720. In one embodiment the controller 722 performs an analysis routine which determines and records the spin echoes, performs FFT analysis to obtain spectral peaks, finds the maximum value of the peaks, and fits the peak values to a formula with three variables: the amplitude and decay time of an exponential, plus a time-independent background. The observed T2 value is the best-fit exponential decay time.

The analysis performed by the controller includes a comparison between the observed T2 value and a previously calibrated or measured T2 value. The analyte is detected by the system when the observed T2 value of the sample differs from that of an analyte-free sample. The previously calibrated T2 value can be determined by measuring a solution of water with the same concentration of nanoparticles as is used for the measurement of the analyte. The T2 of the water is influenced by the concentration of nanoparticles. The T2 is also influenced by analyte binding to the nanoparticles and occupying the high-gradient region around the nanoparticles. In the preferred embodiment, the nanoparticle concentration is controlled by formulation of the solution. The T2 values of the solution without analyte, and with various concentrations of the analyte, are also known by prior calibration.

In one embodiment the nanoparticles are dissolved or suspended in a water medium. The nanoparticles have a superparamagnetic magnetite core with a diameter of 8 nm, surrounded by a shell with a diameter of 50 nm. Antibody molecules (or other binding or attracting mechanism as described herein) specific to the analyte are bound to the shell. When the nanoparticles are in the sample 714, the core is magnetized by the field applied by the magnet 712. The magnetized core produces a local dipole field which adds to the applied field. The resulting net field includes spatial gradients of up to 0.1 T/nm, within a region extending radially from the surface of the nanoparticle to about 20 nm from the surface. The nanoparticles are most effective for detection and measurement purposes in low concentrations of about 1:10000 in water. That results in very little consumption of the nanoparticles per test. In one embodiment the magnet 712 of the magnetic resonance system 700 uses a permanent magnet for this purpose. The permanent magnet requires no power, may be made arbitrarily compact, and is economical. Most prior magnetic resonance systems employed electromagnets or superconducting coils to generate the magnetic field. It is not feasible to arbitrarily reduce the size of electromagnets or superconducting magnets. If an electromagnet is scaled down in size, the magnetic field scales proportionately. If the field is held constant, then the current density in the electromagnet coils must be increased. Current density can not be increased arbitrarily because of a fundamental limit, the conductivity of copper. Above a certain current density limit, roughly 100 amps/cm$^2$, the coils must be water-cooled. Above a second limit, roughly 200 amps/cm$^2$, the coils self-destruct. Small, high-field, steady-state copper coils are not feasible.

It is likewise not feasible to reduce the size of superconducting magnets arbitrarily. Superconducting coils may be made much smaller and more powerful than nonsuperconducting coils, and can carry high current densities. However, superconducting coils must be surrounded by a vacuum-insulated cryostat, usually having multiple shells maintained at different cryogenic temperatures. Also, the various shells are mechanically and thermally interconnected by support struts. It is not possible to make the cryostat arbitrarily thin because of the thermal conductivity of support members. The cryostat limits the miniaturization feasible in superconducting magnets.

Permanent magnets have neither of these defects. A given magnet design using permanent magnets will scale precisely, with no change in geometry or field or field quality, to arbitrarily large or small dimensions. The only fundamental limitation is the ferromagnetic domain size, about 1 micron. By designing permanent magnet systems, the magnets may be scaled to a size determined by the sample volume, the RF coil properties, or other parameters of the system, rather than forcing the other parameters to comply with the magnet scale. As a result, it is feasible to miniaturize the entire electromagnetic system. This leads to improved detection sensitivity in smaller sample volumes, reduced cost and weight of the sensor portion of the system, and reduced RF power required.

Figure 9:
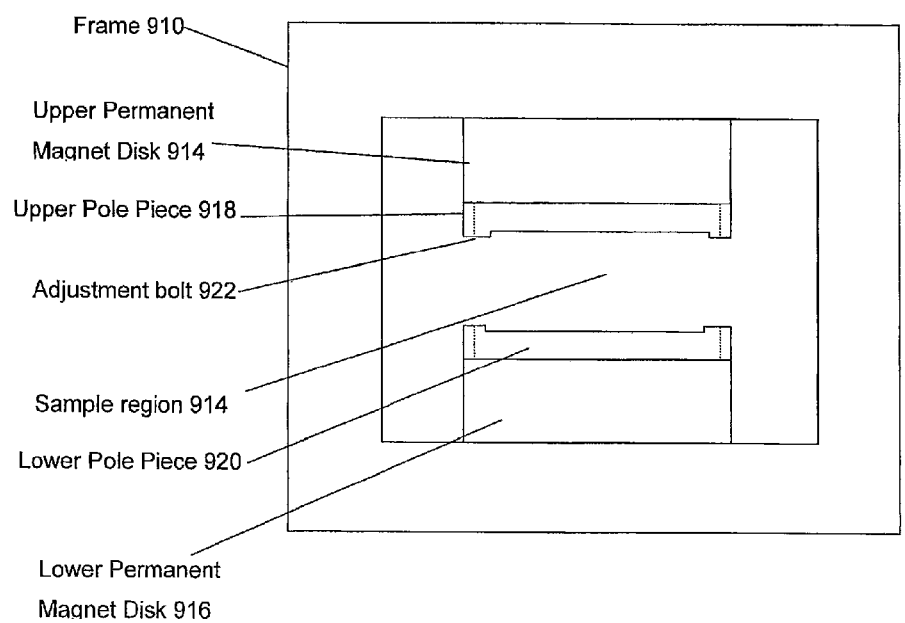
FIG. 9 is a schematic representation of one embodiment of a magnet.

One embodiment of the magnet 712 is depicted schematically in cross section in FIG. 9. The magnet includes a frame 910, such as a hollow steel frame. In one embodiment, the height H of the frame is less than 50 cm and may be less than 5 cm. The width W can also be less than 50 cm and can be less than 5 cm. An upper permanent disk magnet 914 is attached to an upper section of the frame, and a lower permanent disk magnet 916, located opposite the upper permanent magnet, is attached to a lower section of the frame. For example, the disks can be mechanically attached using screws or bolts and/or they can be attached with an adhesive. A disk shaped upper pole piece 918 is located atop the upper permanent magnet and opposite a disk shaped lower pole piece 920 located atop the lower pole piece. Around the periphery of each pole piece are eight fine-threaded holes with adjustment bolts, which may be varied to improve the uniformity of the field. The magnet is assembled by bolting the frame together, sliding the permanent magnet disks into position, sliding the pole pieces into position, and then shimming. The permanent magnet disks are very strongly attracted to the steel frame, and the pole pieces are very strongly attracted to the permanent magnet disks. The attractions, and resulting friction among the various contacting members, provide mechanical stability to hold the assembly together. Further robustness may be obtained by applying clamps or adhesives to the magnet disks or pole pieces, preferably not interfering with field shimming or magnetic resonance measurements. Forces on permanent magnet components are strong and potentially dangerous. Not shown are jigs and tools used to control the assembly process in view of the strong forces involved.

Shimming is the process of adjusting a magnet, such as magnet 712, to produce the necessary uniformity. As built, most magnets provide insufficient uniformity due to manufacturing tolerances. Shimming consists of measuring the field distribution, adjusting built-in parameters of the magnet, and repeating until the desired uniformity is achieved. In one embodiment a simple shimming design is utilized which focuses on the most important field parameters, rather than providing an exhaustive set of parameters of which most are never needed.

First, the magnetization of the two permanent magnet disks is equalized. Based on the observed axial gradient, one or more thin ferromagnetic sheets are affixed by magnetic attraction circumferentially around only the stronger of the two magnets. Iterative adjustment of the number and thickness of the sheets results in near-perfect negation of the axial gradient. The sheets may then be secured by clamps or adhesives.

Then, one or more of the miniature bolts, for example bolt 922, in the periphery of the pole pieces are adjusted. These bolts press against the permanent magnet disks to slightly rock the pole pieces as needed to negate transverse field gradients. Either or both pole pieces may be adjusted, depending on the details of the observed field. Final adjustment of the various bolts results in near-perfect negation of transverse gradients.

Typically the shape of the pole pieces need not be altered, although they can be demounted and their shape revised if needed to achieve the desired field. Alternatively, the spacing between the pole pieces may be reduced slightly by tightening all of the bolts around both pole pieces. Such an adjustment is almost equivalent, magnetically, to adjusting the depth of the pole piece relief step.

To fabricate the magnet parts, powdered metals such as iron or steel can be placed inside a mold of desired shape.

Then in the press pressure and heat are applied to generate the final part. While only small parts can be made by this technique, mass manufacturing can be achieved. Alternatively machining can be used to make the individual parts.

The pole pieces can be designed to provide the highest field uniformity and field volume for sample testing, with the constraint that the gap be sufficient for inserting and tuning the magnetic resonance sample coil. Design constraints include the maximum field in the pole pieces to limit saturation, minimum number of shimming parameters to achieve target field uniformity, and use of low-cost commercial permanent magnet components where possible.

The permanent magnet material provides very high magnetization density, but is temperature sensitive. In applications where the frequency may be adjusted to the field, thermal drift of the magnetic field is not a problem. For precision T2 measurements, however, it is necessary to stabilize the magnetic field. A temperature-controlled enclosure can be used. In one embodiment, the enclosure can be built using foam insulation and a pair of patch heaters. A thermocouple sensor and controller complete the arrangement.

Figure 10:
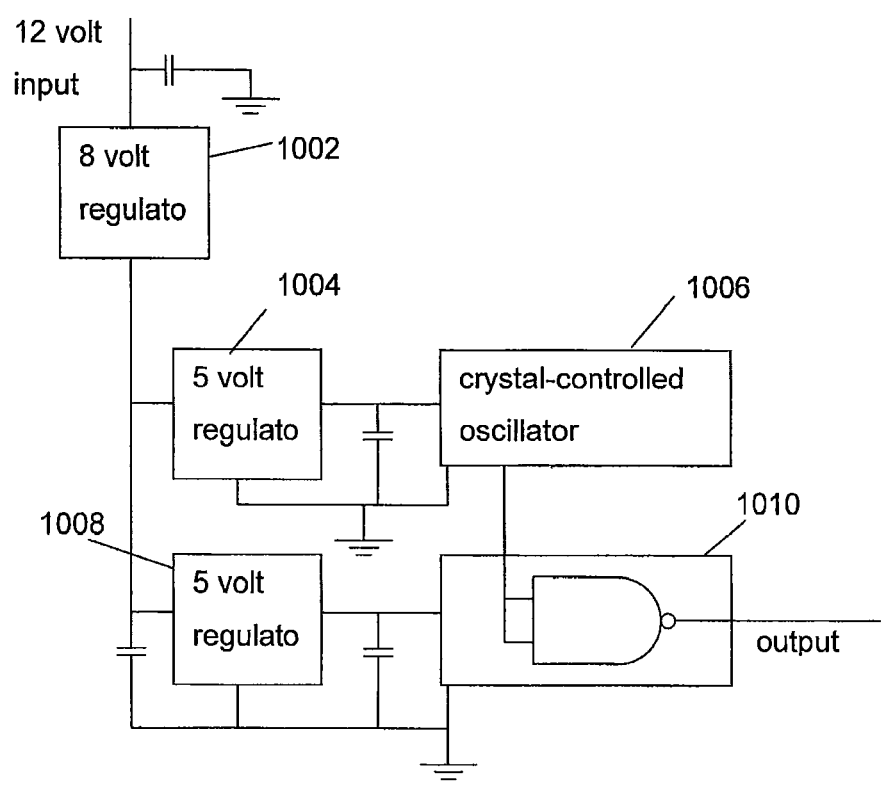
FIG. 10 is a circuit diagram of a buffered oscillator.

Precise determination of T2 using the CPMG procedure is enhanced with an extremely stable local oscillator with minimal phase noise on a time scale of at least the spin echo spacing. Even high-cost crystal oscillators usually do not provide sufficient stability due to the noisy computer power lines. Sufficient stability can be obtained using inexpensive integrated crystal oscillators by buffering both the DC power input, and the RF clock output. Such an arrangement is depicted schematically in FIG. 10. In one embodiment the oscillator shown in FIG. 10 is used in the pulse generator 718 of FIG. 7. In general, the DC (direct current) power input is buffered by wiring two or more voltage regulators in series. The circuit depicted in FIG. 10 includes a first voltage regulator 1002 (for example an 8 volt regulator which receives a +12V input). A second voltage regulator 1004 receives the output of the first voltage regulator and provides its output to the oscillator 1006 (for example, a 5 volt regulator, receiving the output of the 8 volt regulator). A third voltage regulator 1008 (for example, a 5 volt regulator) can also receive the output of the first voltage regulator and can provide its output to a digital logic gate 1010 with high speed and high source isolation, such as the 74F3037 line driver NAND (available from Philips Semiconductors and others). The digital logic gate 1010 buffers the output of the oscillator.

The magnetic resonance system 700 (FIG. 7) interacts with the sample using the antenna 716 which, in operation, is electromagnetically coupled to the precessing nuclei of the sample. In one embodiment the coil is mounted in a modular, interchangeable platform to enable changing the sample size, replacing the coil in case of contamination, or other changes needed.

The antenna may be encapsulated in a contamination-resistant material. Contamination is a serious issue when multiple samples bearing multiple diseases or toxins are to be tested. Prior antennas are difficult to clean because they are highly convoluted geometrically and include non-hygienic insulator and conductor materials. Encapsulation of the antenna can resolve this issue. For example, the antenna could be a copper coil embedded in a hollow cylindrical Teflon form so that any contamination coming from the sample container would encounter only a Teflon surface, never the actual conductor. Since Teflon is non-absorbing and relatively easy to clean up, contamination issues are greatly reduced. Also, the encapsulated antenna would be more stable and mechanically rugged than a freely mounted coil. Magnetic resonance signals from an element in the encapsulant, such as deuterium or fluorine, may be used to control a frequency or a magnetic field.

Cancellation of noise, interference signals, baseline offsets and other background effects can be improved by performing magnetic resonance measurements multiple times with various RF phases alternated. This can be implemented under the control of the controller. For example, the excitation may be alternated between positive and negative phase rotation of the spins during RF pulses. During signal processing by the controller, the phase of the receiver oscillator can also be rotated by 90 degrees or its multiple. Analysis software in the controller controlling these phase alternations also performs the corresponding addition or subtraction of the digitized data to accumulate the desired signal while canceling backgrounds.

Various user interfaces can be provided with the system. For example, the system 700 depicted in FIG. 7 can carry out measurements to detect a selected analyte or analytes and report the results by issuing an alarm if detected or provide a visual indication or report via the user interface 724. In one version, the operator inserts a mixed sample into the system and presses a single button on the user interface to initiate a previously prepared series of instructions for the controller to carry out and analyze the sample. If more than one analyte is to be searched for, the instructions automatically direct the mixing of nanoparticles sensitized to each analyte and carries out the measurements sequentially. In another version of the instrument, a mechanical or optical switch senses the insertion of the sample into the magnetic resonance system, and automatically initiates the measurement sequence.

In one embodiment, a T2 change is the primary indicator that analyte is present. To check for drifts or errors which could affect the T2 measurement, the system can compare the measured T2 of the sample, with that of a sealed calibration sample having a previously measured T2 value. The sealed sample may contain copper sulfate in water, mineral oil, or other liquid having a stable T2 for comparison. Alternatively, the sealed calibration sample can be periodically measured.

A wide diversity of mechanisms for presenting the sample into the magnetic resonance system can be used. The sample, comprising liquid medium, analyte, and nanoparticles, can be mixed in a container such as a glass NMR tube, a plastic tube or vial, a disposable container such as a plastic microcentrifuge tube or flask, or other suitable container. An advantageous polymer is PEEK (polyetheretherketone) due to its toughness, intertness, and machinability. The container may be coated with a material to prevent nanoparticles from adhering to the walls, clumping, or precipitating out of the mixture. For example, the coating may be a protein such as BSA (bovine serum albumin). The container including the sample may be inserted, manually or by a mechanical feeder, into the magnetic resonance system. Alternatively, a fixed container in the magnetic resonance system may be used for multiple sample measurements by inserting sample liquids into the container, for example by pumping the sample or its ingredients through tubes into the container. After the measurements, the sample is then drawn from the fixed container using pumps, tubes, valves, and related fluid flow devices. A washing or rinsing step can be carried out between samples. Ultraviolet treatment of reservoirs holding distilled water and nanoparticles can be carried out to prevent bacteria formation. Alternatively, a fungicide such as sodium azide can be mixed in the distilled water in trace quantities to prevent growth of bacteria and algae in the water.

Figure 11:
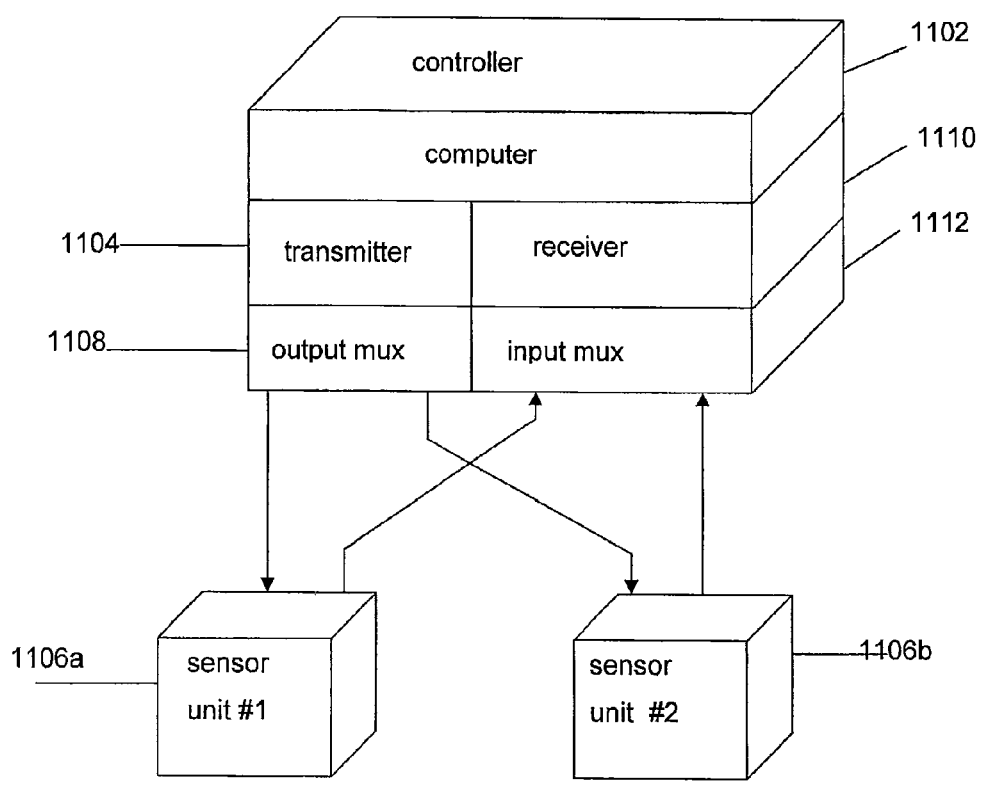
FIG. 11 is a schematic illustration of an installation having one controller and multiple sensor units.
Figure 12:
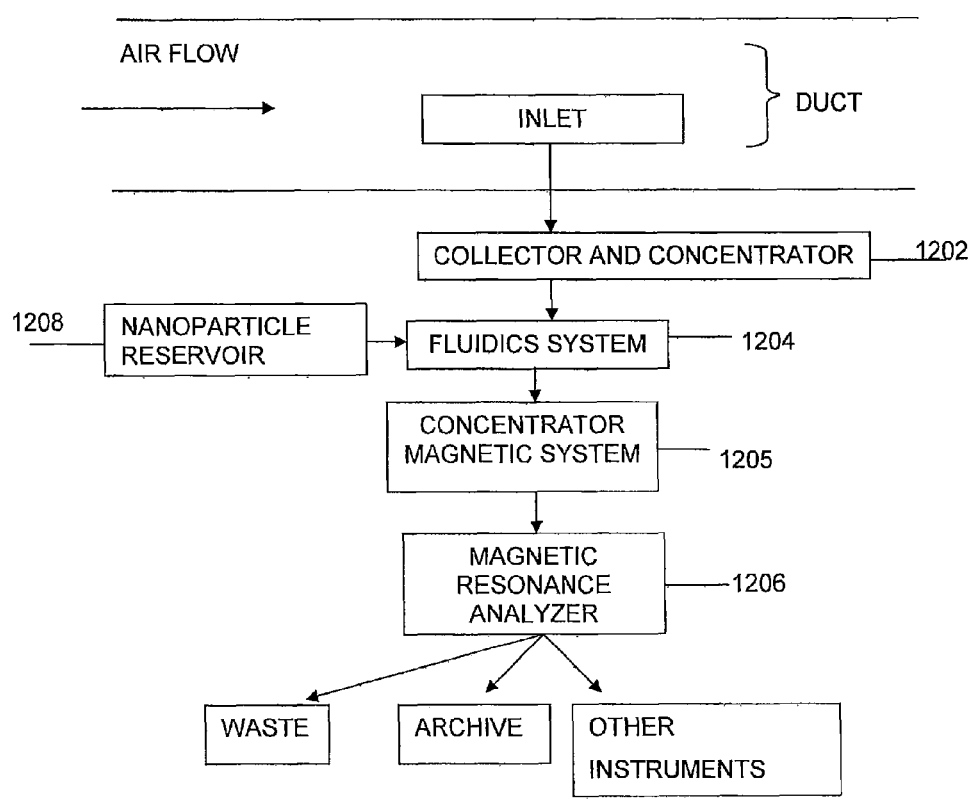
FIG. 12 is a schematic depiction of an analyzer system suitable for use with an HVAC system.
Figure 13:
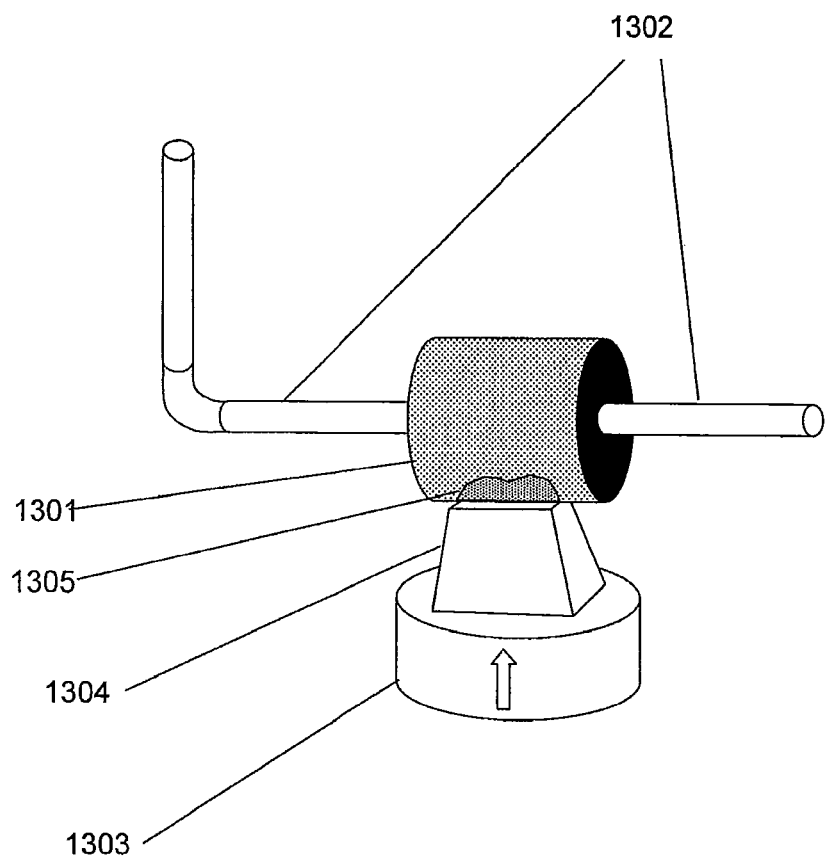
FIG. 13 is a representation of a concentrator magnet system.
Figure 16:
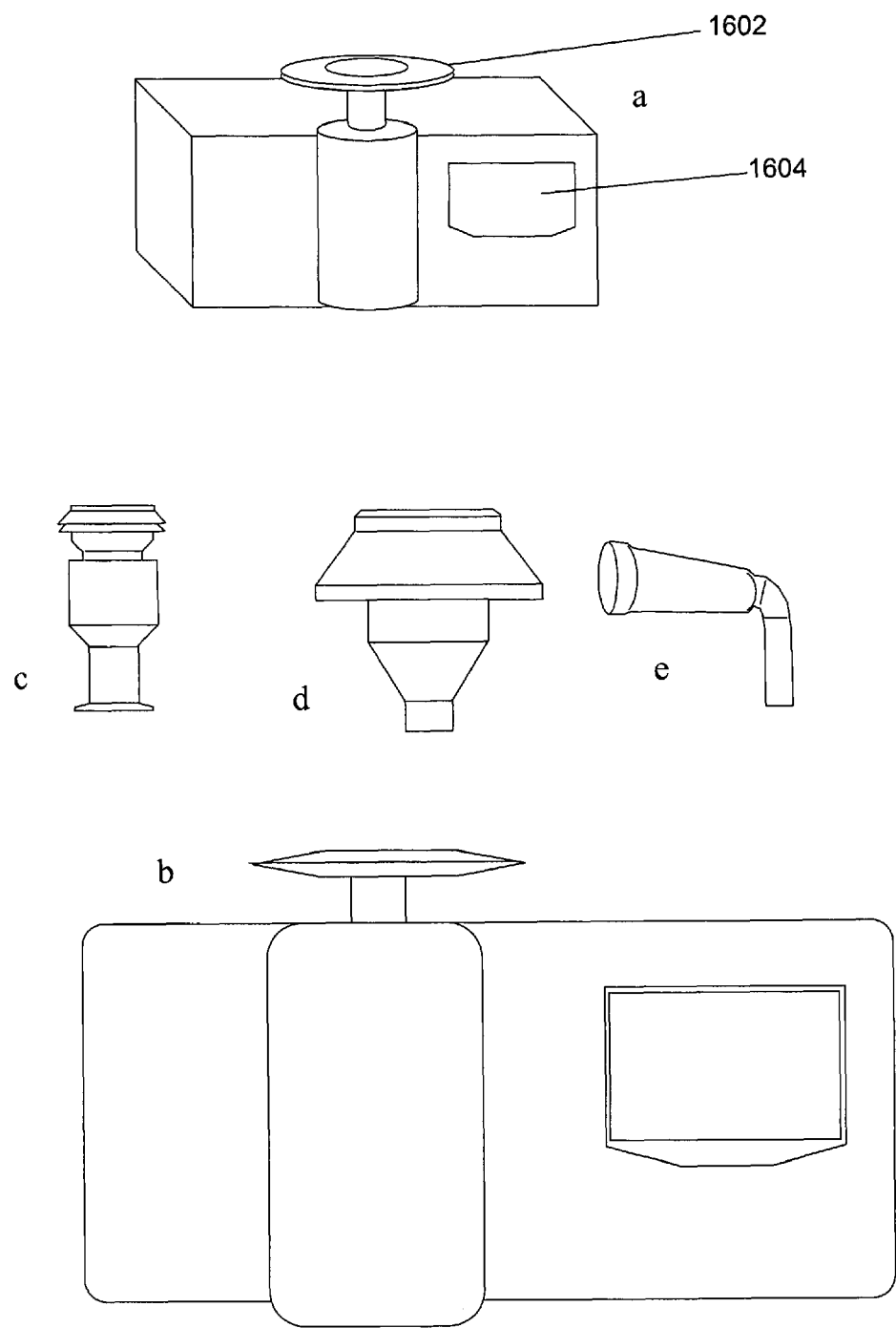
FIGS. 16a-e depict an embodiment of a fixed installation system and three collector intakes.

In one embodiment depicted schematically in FIG. 11, multiple sensor units are connected to a single controller. For example, an automated, fixed-site system may consist of one central controller 1102 with power supplies and a pulse generator or transmitter, connected by cables to multiple remote sensor heads 1106 a and b. Though only two sensor heads are depicted, more can be used. Each head 1106 includes a sample preparation apparatus along with selected nanoparticles, a magnetic resonance magnet, a preamplifier and a coil, for example as were described in connection with FIG. 7. RF power pulses are routed to the sensor units through an output multiplexer 1108 which is controlled by the controller 1102. Signals from the sensor units are routed to the receiver 1110 through the input multiplexer 1112, also controlled by the controller. Interconnects are preferably by coaxial cable. Alternatively, each sensor unit may include an RF amplifier. When the RF amplifier is located at the sensor unit, the interconnects do not carry high power RF pulses and thus may be wireless, fiber optics, or other communication means as well as coaxial cable. The elements of the system depicted in FIG. 11 operate in the manner described above.

In one embodiment, particulate matter suspended in air may be drawn from free air, HVAC ducts, interior spaces such as shopping malls, subway trains and other mass transit areas, or any other air system to test for diseases or terrorist attack. (HVAC stands for heating, ventilation, and air conditioning.) Collection preferably includes drawing particulate matter into the system or concentrating particles from the air into the liquid medium. FIG. 12 shows a schematic of such a monitor system. The collector 1202 can be situated within a duct or in any other area to be monitored, and can include a shroud (not shown) to exclude dirt and insects. The collector 1202 can include an electrostatic concentrator to attract analyte or sample material. A fluidics system 1204 transports the analyte from the collector 1202 to the concentrator magnet system 1205 where the sample is exposed to a non-uniform magnetic field as has been described above. Alternatively, the concentrator magnet system can produce a uniform field. The fluidic system then transports the sample from the concentrator magnet to the sample area of the magnetic resonance analyzer or system 1206. The magnetic resonance system 1206 can be the system described in connection with FIG. 7. The fluidics system 1204 can include an automated microfluidic mixer to mix analyte with a liquid, such as the water medium and with nanoparticles configured for the one or more analytes to be detected. A reservoir of the nanoparticles and the water 1208 can also be part of the fluidics system. The mixed sample is then transferred by the fluidics system to the concentrator magnet system 1205 where the sample is exposed to a non-uniform magnetic field. The fluidic system then transports the sample to the sample area of the magnetic resonance system where measurements are made. In one embodiment a fluidic transport system is in communication with the mixer and extends into the sample area. Depending on the measurement results, the sample may be dumped into a waste container, stored as archive material, or sent to secondary analysis systems. The waste water may be recycled to be used again by passing through a filter.

FIGS. 13 and 14 are schematic representations of magnetic concentrator systems. The system depicted in FIG. 14 is one embodiment of a system which can be used as magnetic concentrator 705 to carry out the methods described herein. The embodiment shown in the figure is a flow cell vessel including an external-type magnetic separation system. A flow cell 1301 contains the nanoparticle-analyte mixture (represented by the light stipple). Tubes 1302 carry the mixture into and out of the flow cell 1301. A permanent magnet 1303 and a flux concentrator 1304 for example, a field-concentrating pole piece, are located in proximity to the flow cell 1301. The magnet 1303 has an associated magnetic field with a direction indicated by the arrow. The flux concentrator 1304 conveys magnetic flux from the magnet 1303 into the flow cell 1301 and produces a non-uniform magnetic field and a strong field gradient throughout the flow cell 1301. A high-field region 1305 (dark stipple) where the field strength is highest is created in the flow cell adjacent to the flux concentrator 1304. The flux concentrator 1304 is shaped in this embodiment so as to produce a roughly linear high-field region 1305 extending along the surface of the flow cell 1301. Nanoparticle-analyte complexes in the fluid mixture are drawn toward the high-field region 1305, thereby increasing the concentration of complexes and enhancing the interaction rate.

FIG. 14 is a combined overhead plan view and an elevation cross-sectional view of a magnetic concentrator system which can be used with the analyzer systems described herein. Centrifuge tubes 1412 and 1413 containing the nanoparticle-analyte mixture (shown in stipple) are placed in the magnet assembly 1411. The magnet assembly 1411 includes a disk-shaped permanent magnet 1414 which is a NdFeB permanent magnet disk with a strength of 42 MGOe and a magnetization direction as indicated by the arrow. Topping the permanent magnet 1414 is a pole piece 1415 which is a steel disk from which six semi-circular notches 1416 have been cut. The pole piece 1415 in cooperation with the permanent magnet 1414 generates a strong, highly non-uniform magnetic field 1417 in the space between the circular notches, and in which the centrifuge tubes 1412 and 1413 are placed. The purpose of the shaped pole piece 1415 is to redirect magnetic flux from the permanent magnet 1414, and emit that flux radially as close to the centrifuge tubes 1412 and 1413 as possible. The outer shell of the magnet assembly 1411 may be steel, to confine the processing region and carry flux back to the permanent magnet 1414. The embodiment shown produces a magnetic field of 0.7 Tesla in the sample volume closest to the pole piece 1415, and falling to about 0.2 Tesla at the opposite side of the centrifuge tube 1412. It will magnetically process six samples simultaneously, converting raw nanoparticle-analyte complexes in solution, to a concentrated deposit of reacted chains, in a few minutes.

FIG. 15 is a graph of magnetic resonance data with and without magnetic processing. The data was collected as part of an experiment to detect biological threat material by measuring the magnetic resonance T2 parameter. The graph shows the change in T2, relative to the initial value, over a 20 hour period for various conditions. The bold (upper) line shows the average of three measurements in which anthrax (bacillus anthraces DNA, plasmid px01, concentration 20 ng/mL) interacts with nanoparticles via selective binding to suitable probes attached to the nanoparticles, and with magnetic processing according to the inventive method. Here the sample mixture was exposed to a nonuniform magnetic field ranging from about 0.8 Tesla at one side of the mixture, to about 0.2 Tesla at the opposite side of the sample, for the duration of the test except when the T2 measurement was actually being made. Also shown as x's are the individual measurements. A substantial signal or T2 change of about 23 milliseconds was observed for the sample having both analyte and magnetic processing. The solid fine line shows the results for the same analyte but with no magnetic processing. Negligible T2 effect is observed. The dotted and dashed lines show the same measurement for control samples having no analyte, with and without magnetic processing. The conclusion from this experiment is that the inventive magnetic processing greatly enhances the detectable magnetic resonance signal from low concentrations of anthrax DNA.

FIGS. 16a-e depict an embodiment of a fixed installation system as described in connection with FIG. 12 and three collector intakes. FIG. 16a is a perspective view and FIG. 16b is a elevation view of the system showing the intake 1602 and a display 1604. The other elements depicted in FIG. 12a are contained within the casing. FIG. 16 c-e depict three inlet options for the system. Once started the controller causes the system to collect samples periodically for analysis. The system can also be operated manually. A user interface may be provided through buttons or a touch screen. The display 1604 can show the status of operation. User access can be controlled through, for example, biometric identification, such as fingerprint identification, or a password.

Figure 17:
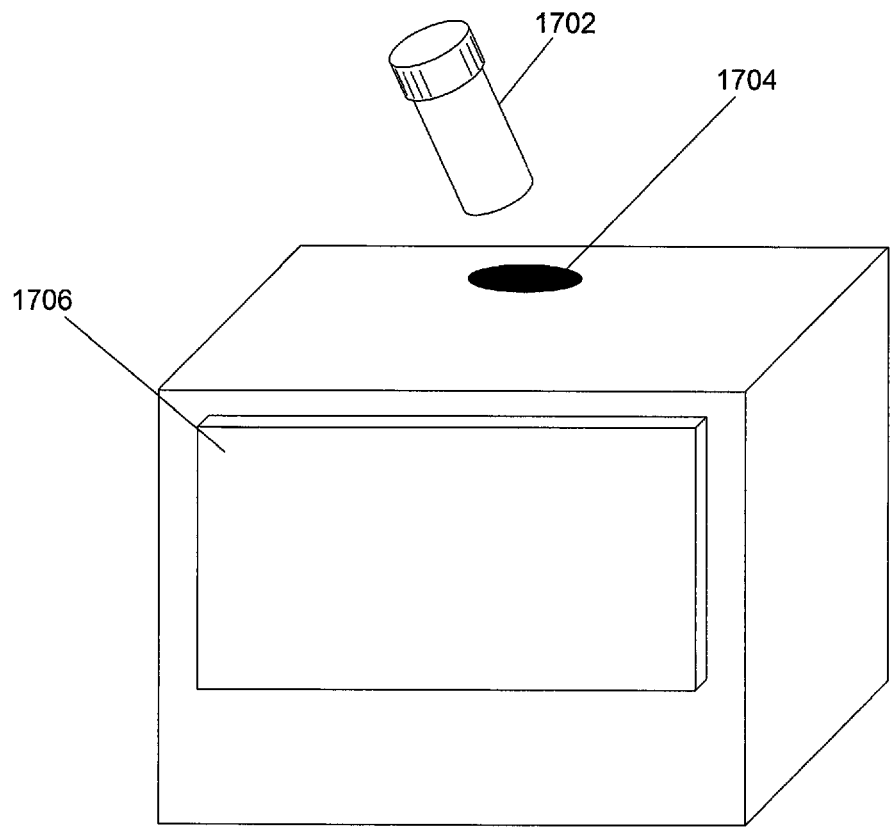
FIG. 17 is a front perspective view of a hand-portable system.

FIG. 17 is a front perspective view of a hand portable system. The system can operate in a single button autonomous operation mode. A sample can be introduced via vials and tubes. A sample in a container 1702 can be introduced into the system through a receptacle or opening 1704 at the top. Inside the system the fluidics system will handle the sample mixing and moving into the NMR system in the manner described above in connection with FIG. 10a. The user interface 1706 can include "biohazard" and "safe" lighted areas on a display screen. To start operation, a start button is provided on the touch screen. The status of system operation is indicated on the screen.

Figure 18:
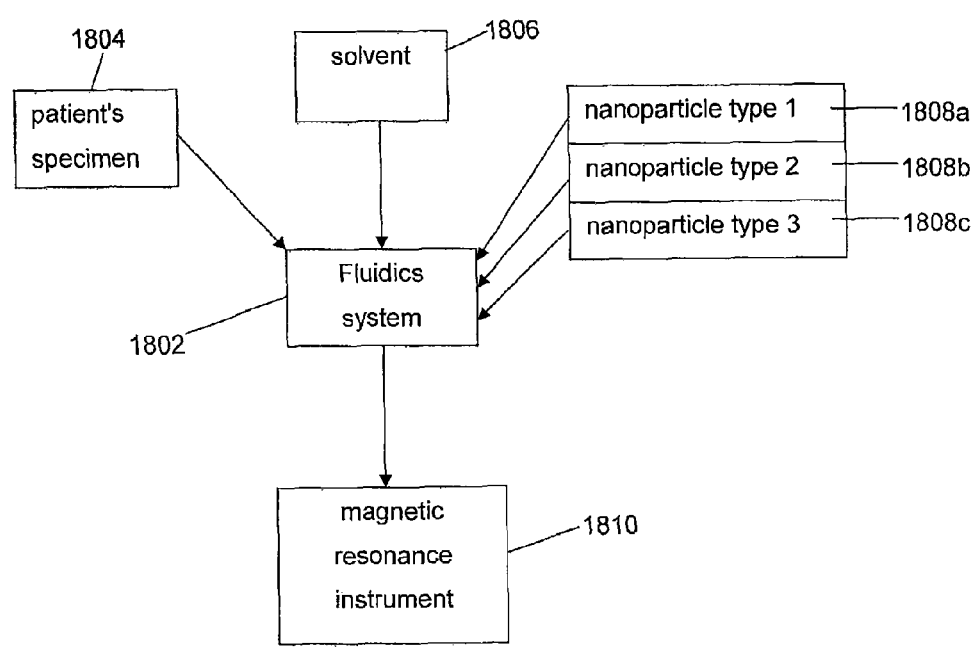
FIG. 18 is a block diagram of a system adapted to a medical diagnostic application.

One embodiment of a system which can carry out or implement the measurement or detection techniques described above for medical diagnostic purposes will now be described with reference to FIG. 18 which is a functional block diagram of an automated sample testing system. For clinical applications, the sample comprises a specimen of material from a patient. The material may include living or dead cellular material such as skin, blood, prions, marrow, hair, biopsy samples, or other tissue; or non-cellular biological material such as saliva, mucous, sputum, intravenous fluid, urine, feces, pus, spinal fluid, and contents of the stomach or intestines; or any other sample material obtained from a human or animal body. Collecting that material comprises a patient or subject producing the material, a clinician extracting the material from the body of a patient or subject, an investigator retrieving sample material from a crime scene or accident, or any other steps resulting in the accumulation of biological material for testing.

Figure 14:
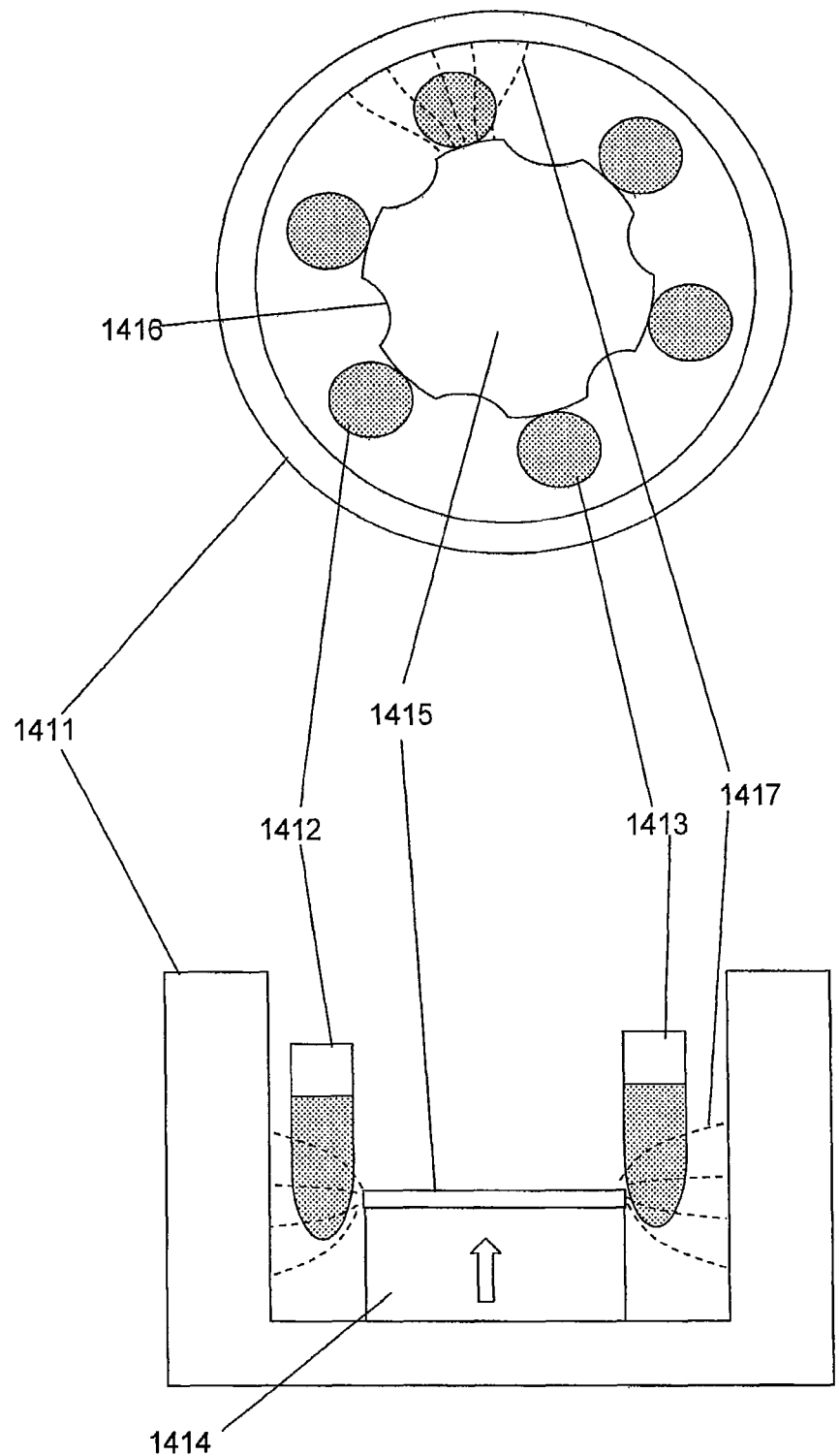
FIG. 14 is a representation of an alternative concentrator magnet system.
Figure 15:
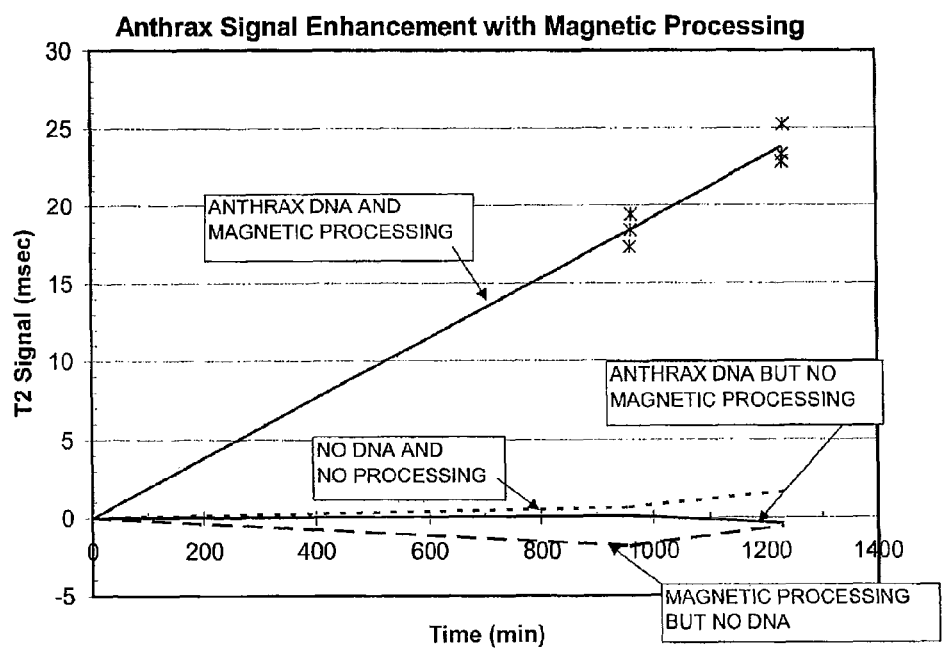
FIG. 15 is a graph of magnetic resonance data with and without magnetic processing.

First, the fluidic system 1802 draws a patient's specimen 1804, or a portion thereof, or a solution thereof, into a mixer which mixes the sample material with a solvent, for example stored in a solvent reservoir 1806, and one or more types of nanoparticles stored in reservoirs 1808a-c. Each type of nanoparticle can be sensitized for one or more chemicals or analytes related to diseases or medical conditions. FIG. 18 shows three nanoparticle types, but any number of nanoparticle types, each sensitized to one or more analytes related to one or more medical conditions can be used. Diseases include communicable pathogens such as viruses and bacteria, and non-communicable diseases such as cancer or hypercholestremia. Chemicals include enzymes or other markers produced by the body, toxins, and drugs. In one embodiment, the user selects the types of nanoparticles to be used in testing a particular patient's specimen. For example, a physician may extract a sample of a patient's blood to check the concentration of a medication so as to control dosage, or guards at an airport or border crossing may take tissue samples of live or dead chickens to check for avian flu. Additional processing steps may include lysing the sample to release DNA or RNA or other components of the sample, heating or cooling the sample, adjusting the pH of the sample, or other steps needed to promote selective reaction between the nanoparticles and the analyte. The mixed sample, or an aliquot thereof, is then transferred into the magnetic resonance system 1810, such as the system depicted in FIG. 7. The system depicted in FIG. 18 can also include a concentrator magnet as was described in connection with FIGS. 7 and 14 above with the samples being exposed to the non-uniform magnetic field while in the magnetic resonance system or prior to the magnetic resonance system. The sample may alternatively be mixed with nanoparticles within a container which is within the magnetic resonance instrument, thereby avoiding the step of transferring the mixed sample, and additional processing steps may be taken while the sample is within the magnetic resonance instrument.

The magnetic resonance instrument then measures signals from the sample, such as the T2 of the sample, and analyzes those signals to determine the presence or absence or concentration of the selected analytes. Then, based on the measurement results, a physician may then diagnose the patient's disease.

In one embodiment of the systems described above, the system detects analyte by measuring signals from the liquid, the signals being related to the magnetic field. Specifically, the signals are sensitive to the distinct magnetic field in the special region around the nanoparticles. When analyte binds to the corresponding antibody or other binding agent, the analyte is caused to remain in the special region, and thus in the distinct magnetic field. The analyte displaces the liquid from that region, so the liquid no longer emits magnetic resonance signals characteristic of the magnetic field in that region. Also, it is important to note that the analyte does not emit magnetic resonance signals, or at least does not emit signals which are similar to those of the liquid. This is because the analyte is held tightly to the solid nanoparticle, causing the analyte to exhibit the short T2 characteristic of solids. Thus, in one embodiment, the analyte, while occupying the special region, does not produce signals that mimic the liquid.

Agglomeration can cause a change in T2 but not T1, whereas both T1 and T2 change in response to increased concentration of nanoparticles. Therefore, a measurement of T1 can be used as a calibration or an independent measure of nanoparticle concentration. In one embodiment, the system measures both the T1 and T2 of the sample, applies analysis relating the T1 value to determine the nanoparticle concentration, and the T2 value to detect analyte. Alternatively, other methods are available to measure the iron content, and hence nanoparticle concentration, in the sample.

The data processing step performed by the controller includes fitting the data for parameters related to the presence of analyte, such as a T2 change in CPMG data. Normally the echo train in CPMG is fit to a single exponential formula, a three-parameter fit for amplitude, time constant, and background. A simple but efficient way to accomplish this is a grid search in which all three parameters are first estimated from the data, and then a three-dimensional grid of values is generated by varying all three parameters above and below the estimated values. Then the best values are selected as the minimum chi-square, or mean squared deviation of the data from the formula. Starting from the best value, a new search grid is again calculated, the deviations calculated, and the best values again derived. This process is repeated a number of times (typically 9) to obtain the best global fit. Optionally, the scale of the grid may be reduced by a factor (typically 0.95) each time it is used, so that the same values are not appearing repeatedly.

The primary subsystems of the magnetic resonance system are the pulse generator, the signal receiver, and the controller. These subsystems may reside on separate boards, interconnected by cables. Alternatively, the subsystems may be integrated as a single circuit on a single computer board. The advantage of the latter is that cable interconnects are not needed, and also that a single time base may be used for all.

The system can be battery powered. The system uses very little power during data acquisition, and can be programmed to use essentially zero power in a sleep mode.

In one embodiment the system also includes a radiation detector interfaced to the controller. The purpose of the radiation detector is to detect radioactive materials in the sample. The radiation detector may be any radiation sensor, preferably sensitive to gamma rays, such as semiconductor, scintillator, and gas-filled counters. The detector may be positioned proximate to the sample collection means, the sample mixing system, or a holding chamber placed downstream of the magnetic resonance system.

Insects such as spiders may obscure the air inlets and collectors. First barrier to entry for these bugs are filters. For outside installations, a slow release insecticide, preferably harmless to humans and pets, can be incorporated. Such insecticides can be implemented along the shaft of the inlet or near the mouth of the inlet.

In one embodiment the systems and methods detect explosives and chemical weapon materials. The systems and methods can perform the detection using nanoparticles as disclosed above, wherein specific binding sites on the nanoparticles bind to the explosive or chemical weapon molecules. Alternatively, the systems and methods can detect explosives or chemical weapon materials by measuring magnetic resonance signals from the sample material itself, without use of nanoparticles. The system may employ the Spin Nuclear Overhauser Effect to detect chemical weapons and explosives. No nanoswitches are required in this case. Another configuration could be a hybrid system incorporating gas chromatography, mass spectroscopy, ion mobility spectroscopy, other analytical techniques, and NMR with or without nanoparticles An advantage of the inventive systems and methods is that confirmation tests may be carried out for certain analytes using the same apparatus. For example, a confirming test for explosives comprises measuring the T1 parameter using a magnetic resonance system, since the T1 for most explosives is extremely long (many seconds). As another example, a confirming measurement for chemical weapons such as nerve agents is a magnetic resonance scan for fluorine or phosphorus based on the characteristic Larmor frequencies of those elements.

In one embodiment the system detects toxins and biological weapons in mail envelopes, by testing particulate matter collected from mail. In this application, the system would preferably include means for extracting particulate matter from envelopes, such as shaking, vibrating, blowing air through the mail piece or compressing the envelopes. The system may include means for cutting envelopes to retrieve powder, preferably only after other sensors had directed suspicion at a particular mail piece.

A preferred embodiment for applications sampling air includes an air inlet, a collector, concentrator and an automated fluidic system. The air inlet includes a filter to exclude dirt and insects, and a cyclone to separate sample particles from air. Inlets may use "impactor" or "pre-separator", or "fractionator" and serves the role of preventing large (e.g., particles with sizes greater than about 10 micrometers aerodynamic diameter) from entering the detector or identifier.

The large-particle fractionator is an integral component in the ambient sampler—it is the combination of the internal nozzle and the plate that is normal to the nozzle. For the HVAC unit or the occupied environment sampler, there could be an optional pre-separator cartridge that is placed downstream of the inlet. In addition, for the ambient sampler, there could be a bug screen that is placed just upstream of the exhaust port. The collector includes concentrator means including a virtual impactor to insert the sample particles into a liquid medium. The fluidic system then mixes the sample with nanoparticles.

In one embodiment the systems and methods are adapted to inspect shipping containers, for example to detect hazardous materials or drugs or microbes among items in a shipping container. The embodiment includes means for drawing air from the interior space of the shipping container, means for collecting or concentrating any material suspended or entrained in that air, means for mixing the material with nanoparticles, and means for presenting that mixture to the magnetic resonance system for testing. The inspection may be carried out by opening a door of the shipping container. Alternatively, the interior air may be drawn through a port or reclosable opening on the shipping container. Further details are provided in Provisional Application Ser. No. 60/669,019, filed Apr. 7, 2005, titled SHIPPING CONTAINER INSPECTION DEVICE.

Those of skill will further appreciate that the various illustrative logical blocks, modules, circuits, and algorithm steps described in connection with the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit without departing from the invention.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such the processor can read information from, and write information to, the storage medium. In the alternative, the storage medium can be integral to the processor. The processor and the storage medium can reside in an ASIC.

The above description of the disclosed embodiments is provided to enable any person skilled in the art to make or use the invention. Various modifications to these embodiments will be readily apparent to those skilled in the art, and the generic principles defined herein can be applied to other embodiments without departing from the spirit or scope of the invention. Thus, the invention is not intended to be limited to the embodiments shown herein but is to be accorded the widest scope consistent with the principles and novel features disclosed herein.

The invention claimed is:

1. A method, for detecting an analyte, comprising the steps of:
   a) mixing a sample containing the analyte with paramagnetic nanoparticles comprising an analyte binding agent, in a known liquid comprising non-zero-spin nuclei, thereby forming a mixture,
   wherein the analyte binding agent can bind to the analyte in the known liquid to form paramagnetic nanoparticle-analyte complexes;
   b) enhancing binding of the paramagnetic nanoparticles comprising an analyte binding agent to the analyte in the mixture by applying an external, non-uniform magnetic field that varies throughout the volume of the known liquid and has maximal field strength in a subvolume of the known liquid,
   wherein the paramagnetic nanoparticles and paramagnetic nanoparticle-analyte complexes are drawn into the subvolume by the non-uniform magnetic field, thereby concentrating the paramagnetic nanoparticles and paramagnetic nanoparticle analyte complexes and enhancing interactions therebetween, except that the non-uniform magnetic field is not applied when the T2 magnetic resonance spin relaxation property measurement is being made; and
   c) measuring a magnetic resonance spin relaxation property of the mixture by:
      i) applying an external uniform magnetic field to the mixture;
      ii) applying one or more radio frequency energy pulses to the mixture in the uniform magnetic field to reorient the bulk magnetization vector of the non-zero spin nuclei in the mixture; and
      iii) detecting the magnetic resonance spin relaxation property of the mixture, wherein the magnetic resonance spin relaxation property is the spin-spin relaxation time (T2);
   wherein a change in T2 in the presence of the analyte compared to the T2 of a negative control mixture that does not include analyte indicates the presence of analyte in the sample,
   thereby detecting the analyte.

2. The method of claim 1, wherein the analyte is selected from the group of molecules, molecular fragments, molecular complexes, viruses, cells, and bacteria.

3. The method of claim 1, wherein the interactions produce at least one paramagnetic nanoparticle-analyte complex bound to another paramagnetic nanoparticle-analyte complex.

4. The method of claim 1, wherein the T2 of the negative control is a value predetermined from a mixture of the known liquid with the nanoparticles.

5. The method of claim 1 further comprising collecting an airborne sample comprising analyte and air; concentrating the analyte into a liquid form; and mixing the concentrated analyte with the paramagnetic nanoparticles and the known liquid.

6. The method of claim 5 wherein the known liquid is water.

7. The method of claim 1 wherein the interactions are selected from the group consisting of an antibody binding with a protein, DNA bonding with complimentary DNA, an antibody binding to an antigen, an oligonucleotide binding with an RNA, a DNA-aptamer binding to a target protein, a DNA-aptamer binding to a target bacteria, a DNA-aptamer binding to a target virus, a DNA-aptamer binding to a target yeast, a DNA-aptamer binding to a target fungus, a protein binding to a target protein, a protein binding to a target bacteria, a protein binding to a target virus, a protein binding to a target yeast, a protein binding to a target fungus, a peptide binding to a target protein, a peptide binding to a target bacteria, a peptide binding to a target virus, a peptide binding to a target yeast, a peptide binding to a target fungus, and a pseudopeptide composed of unnatural amino acids binding with a target, a small molecule binding to a target.

8. The method of claim 1, wherein the external, non-uniform magnetic field is applied through a permanent magnet.

9. The method of claim 8, where the external, non-uniform magnetic field has a field strength in the range of 0.01 Tesla to 20 Tesla.

10. The method of claim 1, wherein the non-zero-spin nuclei are hydrogen atoms.

11. The method of claim 1, wherein the paramagnetic nanoparticles have an overall diameter of 50 nm.

* * * * *